United States Patent
Chow et al.

(10) Patent No.: US 11,464,838 B2
(45) Date of Patent: Oct. 11, 2022

(54) OPTIMIZED CANCER STEM CELL VACCINES

(71) Applicant: COLORADO STATE UNIVERSITY RESEARCH FOUNDATION, Fort Collins, CO (US)

(72) Inventors: Lyndah Chow, Fort Collins, CO (US); Steven W. Dow, Littleton, CO (US); Amanda M. Guth, Fort Collins, CO (US); Daniel P. Regan, Fort Collins, CO (US)

(73) Assignee: COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 176 days.

(21) Appl. No.: 15/562,710

(22) PCT Filed: Apr. 1, 2016

(86) PCT No.: PCT/US2016/025596
§ 371 (c)(1),
(2) Date: Sep. 28, 2017

(87) PCT Pub. No.: WO2016/161309
PCT Pub. Date: Oct. 6, 2016

(65) Prior Publication Data
US 2018/0085445 A1    Mar. 29, 2018

Related U.S. Application Data

(60) Provisional application No. 62/141,696, filed on Apr. 1, 2015.

(51) Int. Cl.
*A61K 39/00* (2006.01)
*C12N 5/095* (2010.01)
*A61K 31/4178* (2006.01)
*A61K 31/453* (2006.01)

(52) U.S. Cl.
CPC ...... *A61K 39/0011* (2013.01); *A61K 31/4178* (2013.01); *A61K 31/453* (2013.01); *C12N 5/0695* (2013.01); *A61K 2039/55555* (2013.01); *A61K 2039/55561* (2013.01); *A61K 2039/55583* (2013.01); *A61K 2039/57* (2013.01); *C12N 2500/90* (2013.01); *C12N 2500/99* (2013.01); *C12N 2501/11* (2013.01); *C12N 2501/115* (2013.01)

(58) Field of Classification Search
CPC .. A61K 39/011; A61K 2300/00; A61K 45/06; A61K 35/00; A61K 35/04; C12N 5/0695; C12N 2500/99; C12N 2501/11; C12N 2501/115; C12N 2500/09; C12N 2500/90
See application file for complete search history.

(56) References Cited

U.S. PATENT DOCUMENTS

| 5,750,119 A * | 5/1998 | Srivastava | A61K 38/19 424/277.1 |
|---|---|---|---|
| 8,975,290 B2 | 3/2015 | Dow et al. | |
| 2003/0022854 A1* | 1/2003 | Dow | A61K 9/1272 514/44 A |
| 2005/0124003 A1* | 6/2005 | Atala | C12N 5/0605 435/7.2 |
| 2009/0142365 A1* | 6/2009 | Kim | A61K 39/0011 424/185.1 |
| 2010/0247623 A1 | 9/2010 | Bystryn | |
| 2012/0064094 A1 | 3/2012 | Chabbert et al. | |
| 2012/0156280 A1 | 6/2012 | Dow et al. | |
| 2012/0189664 A1 | 7/2012 | Yu | |

FOREIGN PATENT DOCUMENTS

| WO | WO-2008052740 A2 * | 5/2008 | ......... A61K 39/0011 |
|---|---|---|---|
| WO | 2010133663 A1 | 11/2010 | |
| WO | WO-2012061120 A1 * | 5/2012 | ......... A61K 39/0011 |
| WO | 2014028274 A1 | 2/2014 | |
| WO | 2014134621 A2 | 9/2014 | |
| WO | WO-2014164464 A1 * | 10/2014 | ....... A61K 39/00117 |
| WO | WO-2014165103 A1 * | 10/2014 | |

OTHER PUBLICATIONS

Nanni et al (Cancer Research, 2007, vol. 67, pp. 11037-11044) (Year: 2007).*
Choonara et al (Biotechnology Advances, 2014, vol. 32, pp. 1269-1282) (Year: 2014).*
Mitchell et al (International Immunopharmacology, 2013, vol. 15, pp. 357-363) (Year: 2013).*
Gertz, American Journal of Hematology, 2015, vol. 90, pp. 347-354 (Year: 2015).*
Cabarcas et al, International Journal of Cancer, 2011, vol. 129, pp. 2315-2327 (Year: 2011).*
Chen et al, PLoS One, 2012, vol. 7, No. 2, e31864, 11 pages (Year: 2012).*
Abstract of Jajosky et al, Clinical and Experimental Metastasis, Feb. 2011, vol. 28, No. 2, p. 198, Abstract No. A112 (Year: 2011).*
Kast and Belda-Iniesta (Current Stem Cell Research & Therapy, 2009, vol. 4, pp. 314-317) (Year: 2009).*
Pollack et al (Journal of Clinical Oncology, 2014, vol. 32, pp. 2050-2058) (Year: 2014).*
Kang and Kang (Stem Cells and Development, 2007, vol. 16, pp. 837-847). (Year: 2007).*
Friedrich et al (Nature Protocols, 2009, vol. 4, pp. 309-324) (Year: 2009).*
Liu et al (Cellular Signalling, 2014, vol. 26, pp. 2773-2781) (Year: 2014).*

(Continued)

*Primary Examiner* — Karen A. Canella
(74) *Attorney, Agent, or Firm* — Polsinelli PC

(57) ABSTRACT

The present invention provides cancer stem cell vaccines useful for treating or preventing a variety of tumors, as well as related methods of producing cancer stem cells and antigens thereof and producing vaccine adjuvants with enhanced activity for use with the stem cell vaccines.

16 Claims, 16 Drawing Sheets

(56) References Cited

OTHER PUBLICATIONS

Wu et al (Journal of Immunotherapy, 2007, vol. 30, pp. 789-797) (Year: 2007).*
Hirchhaeuser et al, Journal of Biotechnology, 2010, vol. 148, pp. 3-15 (Year: 2010).*
Pellegata et al ('Dendritic Cell Vaccines for Cancer Stem Cells', In: Cancer Stem Cell Methods in Molecular Biology, 2009, John Yu, Ed., vol. 568, pp. 233-247) (Year: 2009).*
Weiswald et al (Neoplasia, 2015, vol. 17, pp. 1-15) (Year: 2015).*
Kim et al (Current Protocols in Cell Biology, 2015, vol. 23, supplement 67, p. 23.10.1 to 23.10.10) (Year: 2015).*
Luo et al (PLoS One, Aug. 2014, vol. 9, No. 8, e103193, 7 pages) (Year: 2014).*
Chando et al., "Biotransformation of Irbesartan in Man," Drug Metabolism and Disposition, vol. 26, No. 5, pp. 408-417.
Dow et al., "Lipid-DNA Complexes Induce Potent Activation of Innate Immune Responses and Antitumor Activity When Administered Intravenously," J. Immunol. 1999; 163:1552-1561.
Ferreiros et al., "Validated Quantitation of Angiotensin II Receptor Antagonists (ARA-II) in Human Plasma by Liquid-Chromatography-Tandem Mass Spectrometry Using Minimum Sample Clean-up and Investigation of Ion Suppression," Ther. Drug Monit. 2007, vol. 29:824-834.
Gonzalez et al., "Fast screening method for the determination of angiotensin II receptor antagonists in human plasma by high-performance liquid chromatography with fluorimetric detection," Journal of Chromatography A, 949 (2002), pp. 49-60.
Higgins et al., "Small molecule CCR2 antagonists," Chemokin Biology—Basic Research and Clinical Application, vol. II, 2007, pp. 115-123.
Koch et al., "Sex and age differences in the pharmacokinetics of alosetron," J. Clin. Pharmacol, 2002, vol. 53, pp. 238-242.
Lu et al., "Quantitation of irbesartan and major proteins in human plasma by mass spectrometry with time-of-flight analyzer," Journal of Pharmaceutical and Biomedical Analysis 54(2011), pp. 100-105.
McCarthy et al. "Determination of losartan and its degradates in COZAAR tablets by reversed-phase high-performance thin-layer chromatography," Journal of Pharmaceutical and Biomedical Analysis 17 (1998) 671-677.
Mirzadegan et al., "Identification of the Binding Site for a Novel Class of CCR2b Chemokine Receptor Antagonists," The Journal of Biological Chemistry, vol. 275, No. 33, Aug. 18, 2000, pp. 25562-25571.
Mitchell et al., "Suppression of Vaccine Immunity by Inflammatory Monocytes," J Immunol 2012 189:5612-5621.
Muth et al., "High Dose Ondansetron for Reducing Motion Sickness in Highly Susceptible Subjects," Aviation, Space, and Environmental Medicine, Jul. 2007, vol. 78, No. 7, pp. 686-692.
Sirota et al., "Use of the Selective Serotonin 3 Receptor Antagonist Ondansetron in the Treatment of Neuroleptic-Induced Tardive Dyskinesia," Am J Psychiatry 2000; 157-287-289.
Yeung et al., Determination of plasma concentrations of losartan in patients by HPLC using solid phase extraction and UV detection, International Journal of Pharmaceutics 204 (2000) pp. 17-22.
Zaks et al., "Efficient Immunization and Cross-Priming by Vaccine Adjuvants Containing TLR3 or TLR9 Agonists Complexed to Cationic Liposomes," J Immunol 2006; 176:7335-7345.
Broocks et al, "Acute intravenous administration of andansetron and m-CPP, along and in combination, in patients with obsessive-compulsive disorder (OCD): behavior and biological results," Psychiatry Research 79 (1998) 11-20.
Xu et al., "Determination of ondansetron and its hydroxy metabolites in human serum using solid-phase extraction and liquid chromatography/positive ion electrospray tandem mass spectrometry," J. Mass Spectrom. 35, 1329-1334 (2000).
Somers et al., "The metabolism of the 5HT3 antagonists, ondansetron, alosetron and GR87442 II: Investigation into the in vitro methods used to predict the in vivo hepatic clearance of ondansetron, alosetron and GR87442 in the rat, dog and human," Xenobiotica, Aug. 2007; 37(8): 855-869.
Zhang et al., "Beneficial effects of ondansetron as an adjunct to haloperidol for chronic, treatment-resistance schizophrenia: A double-blind, randomized, placebo-controlled study," Schizophrenia Research 88 (2006) 102-110.
Zullino et al., "Ondansetron for Tardive Dyskinesia" Letter to the Editor, The American Journal of Psychiatry, Apr. 1, 2001, vol. 158, Issue 4, pp. 657-658.
Jones et al., "Protection against pneumonic plague following oral immunization with a non-replicating vaccine," Vaccine, Aug. 16, 2010, vol. 28(36), 5924-5929.

* cited by examiner

OPTIMIZED CANCER STEM CELL VACCINES

CROSS REFERENCE TO RELATED APPLICATIONS

This application claims priority to U.S. Provisional Application No. 62/141,696, filed on Apr. 1, 2015, which is incorporated by reference herein in its entirety.

FIELD OF THE INVENTION

This invention relates to novel cancer stem cell vaccines and related methods of treating and preventing cancer, as well as methods of producing cancer stem cells and antigens thereof useful in preparing the cancer stem cell vaccines.

BACKGROUND OF THE INVENTION

Cancer stem cells (CSCs) are tumor cells that possess characteristics associated with normal stem cells, including the ability to give rise to all cell types found in a particular tumor sample. CSCs are tumorigenic and may generate tumors by self-renewal and differentiation into multiple cell types, which are hallmark characteristics of stem cells. In addition, tumor drug resistance is believed to be closely related to many properties of CSCs, such as quiescence, specific morphology, DNA repair ability and overexpression of anti-apoptotic proteins, drug efflux transporters and detoxifying enzymes. Thus, even with treatment, CSCs cells are believed to persist in tumors and can thereby cause tumor relapse and/or metastasis following the completion of therapy. Therefore, there is a need in the art for therapies targeted specifically at CSCs for improving survival and enhancing quality of life of cancer patients.

BRIEF SUMMARY OF THE INVENTION

The invention includes a multi-component vaccine that specifically targets cancer stem cells for immune elimination. In particular embodiments, the vaccine components comprise: a liposomal-TLR 9 agonist adjuvant, a monocyte migration blocking drug, and a mixture of cancer stem cell antigens purified from in vitro grown cancer stem cells. In particular embodiments, the vaccine components comprise: a liposome-TLR-9 agonist adjuvant containing a cellulose derivative with carboxymethyl groups, such as carboxymethyl cellulose, a monocyte migration blocking drug, and a mixture of cancer stem cell antigens purified from in vitro grown cancer stem cells vaccine. In particular embodiments, the cancer stem cell vaccine is administered at weekly to monthly intervals as a therapeutic treatment for a number of different cancer types. The vaccine is designed to have a broad spectrum of activity against a number of different, unrelated cancer types that all contain cancer stem cells. In certain embodiments, the vaccine elicits immune responses against certain specific proteins only expressed (or overexpressed) by tumor cells grown under stem cell conditions in vitro, e.g., conditions described herein. In particular embodiments, the vaccine elicits immune responses against unique 40 kD and 250 kD proteins expressed by cancer stem cells but not by tumor cells grown under conventional tissue culture conditions.

In one embodiment, the present invention includes a tumor vaccine comprising: one or more cancer stem cell (CSC) antigens; and a vaccine adjuvant. In certain embodiments, the tumor vaccine further comprises a monocyte migration inhibiting drug, or a small molecule antagonist of a C—C chemokine receptor type 2 (CCR2). In particular embodiments, the monocyte migration inhibiting drug is losartan or ondansetron. In certain embodiments, the tumor vaccine further comprises a cellular adhesion agent. In particular embodiments, the cellular adhesion agent is carboxymethyl cellulose or a polyethylene glycol. In certain embodiments, the tumor vaccine comprises: one or more cancer stem cell (CSC) antigens; a vaccine adjuvant; a monocyte migration inhibiting drug, or a small molecule antagonist of a C—C chemokine receptor type 2 (CCR2); and a cellular adhesion agent. In certain embodiments, the one or more cancer stem cell antigens are prepared from tumor cells grown in vitro under conditions that promote growth of tumor cells having one or more characteristic of a CSC. In particular embodiments, the adjuvant is a cationic liposome-DNA complex or a cationic liposome-DNA-pIC complex. In certain embodiments, the monocyte migration inhibiting drug is losartan, ondansetron or an antagonist of the CCR2 polypeptide is RS102895.

In a related embodiment, the present invention includes a method of treating or preventing a tumor or cancer, comprising providing to a subject in need thereof an effective amount of a tumor vaccine described herein. In particular embodiments, the subject is a mammal, e.g., a human. In certain embodiments, the subject has been diagnosed with a tumor or is considered to be at risk of developing a tumor or tumor metastasis. In particular embodiments, the tumor is an epithelial tumor (e.g., a breast cancer or a colon carcinoma) or a mesenchymal tumor (e.g., a melanoma, a soft tissue sarcoma, or an osteosarcoma). In particular embodiments, the tumor vaccine induces an immune response to the tumor in the subject. In particular embodiments, the immune response comprises a T cell response and/or a B cell response.

In further related embodiments, the present invention includes a method of producing cancer stem cells (CSCs), comprising culturing tumor cells in vitro under conditions that promote growth of tumor cells having one or more characteristic of a CSC. In particular embodiments, the tumor cells are cultured in serum-free medium, optionally serum-free DMEM-F12 medium supplemented with 1× B-27 mix and L-alanyl-L-glutamine (e.g., Glutamax™), under non-adherent conditions, in the presence of a fibroblast growth factor (FGF), epidermal growth factor (EGF), or insulin-like growth factor (IGF).14. In particular embodiments, the serum-free medium comprises the FGF (FGF) or EGF. In particular embodiments, the serum-free medium comprises basic FGF and/or EGF. In certain embodiments, the medium comprises insulin, selenium and/or transferrin. In particular embodiments, the tumor cells are cultured under non-adherent conditions. In particular embodiments, the tumor cells have increased expression of CD90, Sca1, CD133, CD117, CD24, CD29, CD34 and/or Oct3/4 following the culturing process. In another related embodiment, the present invention includes CSCs produced by a method described herein.

In a related embodiment, the present invention includes a method of preparing cancer stem cell (CSC) antigens, comprising: culturing tumor cells by a method described herein for a time sufficient to produce CSCs; lysing the tumor cells following the culturing, wherein the lysed cells release the CSC antigens; and collecting CSC antigens released by lysing the tumor cells. In particular embodiments, the lysing comprises freeze-thawing the tumor cells, followed by sonication. In another related embodiment, the present invention includes CSC antigens produced by a method described herein.

In yet another related embodiment, the present invention includes a population of cancer stem cells (CSCs), wherein the CSCs have increased expression of CD90, Sca1, CD133, CD117, CD24, CD29, CD34 and/or Oct3/4 as compared to tumor cells from which the CSCs were derived.

BRIEF DESCRIPTION OF THE DRAWINGS

FIG. 6B).

DETAILED DESCRIPTION OF THE INVENTION

Figure 1:
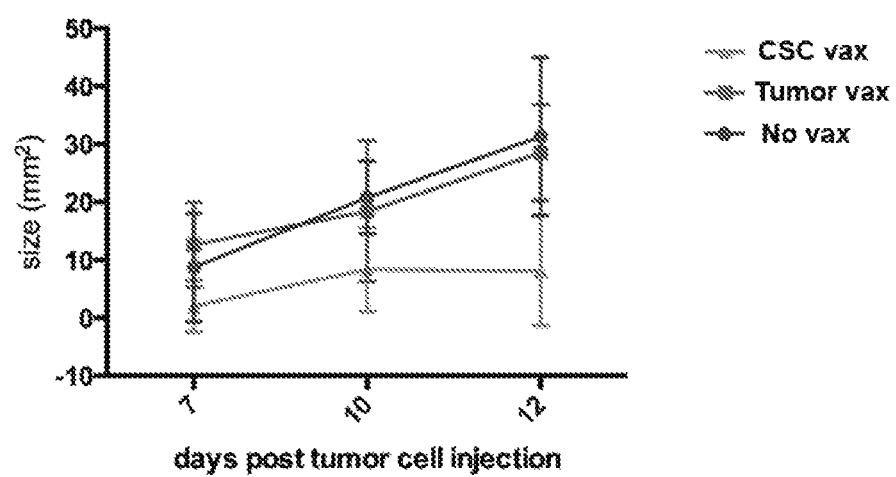
FIG. 1 is a graph showing the effects of therapeutic immunization with CSC vaccine in mice with established colon carcinoma tumors. Mice (n=5 per group) with established subcutaneous CT26 tumors were immunized with the CSC vaccine (CSC vax; triangle) prepared from CT26 cells grown under stem cell conditions, or with a conventional tumor vaccine (Tumor vax; square) or were unvaccinated (No vax, circle). The conventional tumor vaccine was prepared using antigens from CT26 tumor cells grown under conventional tissue culture conditions, which does not enrich for cancer stem cells. In fact, cancer stem cells are very rare in tumor cell lines grown under conventional tissue culture conditions. Vaccinations were repeated s.c. weekly. Tumor dimensions were determined at 3-day intervals. Immunization with the CSC vaccine triggered significant inhibition of tumor growth, compared to animals immunized with a conventional tumor vaccine. The stem cell and conventional tumor vaccines were prepared by freeze-thaw lysing and sonicating tumor cells to prepare tumor lysates, then combining the lysate with cationic liposome and non-coding plasmid DNA adjuvant. The vaccines also contained 250 ug/ml of the specific CCR2 antagonist RS102895 as a vaccine enhancing agent. Each mouse received a vaccine containing 50 ug tumor lysate in 200 ul total vaccine volume with 100 ul liposome-DNA adjuvant, administered SC.

The present invention relates, in part, to the identification of cell culture conditions that induce the generation of cancer stem cells (CSCs) in vitro. Under normal tissue culture conditions, CSCs are very rare in tumor cell lines. However, as demonstrated in the accompanying Examples and figures, tissue culture conditions and methods of the present invention may be used to optimize and enhance the generation of CSCs, thus producing tumor cell cultures having a higher percentage of CSCs than previously produced.

In a related aspect, tumor cell lines cultured according to the methods described herein, which induce the generation of CSCs, are used to prepare tumor antigens enriched for CSC antigens (also referred to herein as CSC antigens).

In a further related aspect, the present invention provides tumor vaccines, e.g., tumor vaccines comprising CSC antigens and/or enriched for CSC antigens as compared to other tumor cell antigens. In particular embodiments, these tumor vaccines, which may also be referred to herein as CSC vaccines, comprise or consist of tumor antigens prepared from cells as described herein (i.e., CSC antigens) and one or more vaccine adjuvants. In particular embodiments, the vaccine adjuvant comprises liposomes complexed to TLR agonists (plasmid DNA and/or polyinosinic polycytidylic acid; pIC), alone or in combination with low molecular weight carboxymethyl cellulose as a cellular adhesive agent to increase uptake and trafficking to lymph nodes, thus enhancing vaccine responses. The CSC vaccines may also include an agent to increase, enhance or amplify cellular immunity.

Illustrative embodiments of these and other aspects of the invention are described in further detail below. However, the invention is not limited to these specific embodiments.

General Methods

The practice of the present invention will employ, unless otherwise indicated, conventional techniques of cell culturing, molecular biology (including recombinant techniques), microbiology, cell biology, biochemistry and immunology, which are within the skill of the art. Such techniques are explained fully in the literature, such as, Molecular Cloning: A Laboratory Manual, third edition (Sambrook et al., 2001) Cold Spring Harbor Press; Oligonucleotide Synthesis (P. Herdewijn, ed., 2004); Animal Cell Culture (R. I. Freshney), ed., 1987); Methods in Enzymology (Academic Press, Inc.); Handbook of Experimental Immunology (D. M. Weir & C. C. Blackwell, eds.); Gene Transfer Vectors for Mammalian Cells (J. M. Miller & M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Manual of Clinical Laboratory Immunology (B. Detrick, N. R. Rose, and J. D. Folds eds., 2006); Immunochemical Protocols (J. Pound, ed., 2003); Lab Manual in Biochemistry: Immunology and Biotechnology (A. Nigam and A. Ayyagari, eds. 2007); Immunology Methods Manual: The Comprehensive Sourcebook of Techniques (Ivan Lefkovits, ed., 1996); Using Antibodies: A Laboratory Manual (E. Harlow and D. Lane, eds., 1988); and others.

Definitions

Unless defined otherwise, all technical and scientific terms used herein have the same meaning as commonly understood by those of ordinary skill in the art to which the invention belongs.

As used herein, the term "effective amount" refers to at least an amount effective, at dosages and for periods of time necessary, to achieve the desired result, e.g., an enhanced immune response to an antigen, a decrease in tumor growth or metastasis, or a reduction in tumor size. An effective amount can be provided in one or more administrations.

As used herein, the term "subject" or "individual" refers to a mammal, e.g., a human, a companion animal (e.g., dog, cat, rodent, rabbit, etc.), a sport animal (e.g., horse, dog, bull, etc.), a farm or food animal (e.g., pig, cow, sheep, goat, etc.), livestock (e.g., donkeys, goats, guinea pigs, sheep, cattle, llamas, etc.), or any other mammalian veterinary animal.

As used herein, the singular form "a", "an", and "the" includes plural references unless indicated otherwise.

Reference to "about" a value or parameter herein refers to the usual error range for the respective value readily known to the skilled person in this technical field. In particular embodiments, reference to about refers to a range within 10% higher or lower than the value or parameter, while in other embodiments, it refers to a range within 5% or 20% higher or lower than the value or parameter. Reference to "about" a value or parameter herein includes (and describes) aspects that are directed to that value or parameter per se. For example, description referring to "about X" includes description of "X."

As used herein, the term "modulating" means changing, and includes positive modulating, such as "increasing," "enhancing," "inducing" or "stimulating," as well as negative modulating such as "decreasing," "inhibiting" or "reducing," typically in a statistically significant or a physiologically significant amount as compared to a control. An "increased," "stimulated" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the amount produced by no treatment as described herein or by a control treatment, including all integers in between. A "decreased," "inhibited" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%), 80%, 85%, 90%, 95%, or 100% decrease in the amount produced by no treatment as described herein or by a control treatment, including all integers in between.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

It is understood that aspects and embodiments of the invention described herein include "comprising," "consisting," and "consisting essentially of" aspects and embodiments.

As used herein, the term "adjuvant" has its conventional meaning, i.e., the ability to enhance the immune response to a particular antigen. Such ability is manifested by a significant increase in immune-mediated protection. An enhancement of humoral immunity is typically manifested by a significant increase (usually about >10%) in the titer of antibody raised to the antigen. Similarly, enhancement of cellular immunity is typically manifested by a significant increase (usually about >10%) in the number of responding CD8+ or CD4+ T cells.

The term "concurrently" is used herein to refer to administration of two or more agents, e.g., CSC antigen and adjuvant, where at least part of the administration overlaps in time. Accordingly, concurrent administration includes a dosing regimen when the administration of one or more agent(s) continues after discontinuing the administration of one or more other agent(s). In particular embodiments, an antigen is administered concurrently with a composition of the present invention.

The terms "tumor," "cancer" and "cancerous" refer to or describe the physiological condition in mammals that is typically characterized by unregulated cell growth. Included in this definition are benign and malignant tumors or cancers as well as dormant tumors or micrometastases. Examples of tumors or cancers include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL);

Hairy cell leukemia; chronic myeloblasts leukemia; and post-transplant lymphoproliferative disorder (PTLD), as well as abnormal vascular proliferation associated with phakomatoses, edema (such as that associated with brain tumors), and Meigs' syndrome.

"Poly(I:C)" is recognized by TLR3 inducing the activation of NF-kB and the production of cytokines. Poly(I:C) is composed of a strand of poly(I) annealed to a strand of poly(C). The size of the strands varies. InvivoGen provides poly(I:C) with two different sizes:
Poly(I:C) (HMW) with a high molecular weight has an average size of 1.5-8 kb, and
Poly(I:C) (LMW) with a low molecular weight has an average size of 0.2-1 kb.

"CpG oligodeoxynucleotides" (CpG ODN; CpG oligos) are short single-stranded synthetic DNA molecules that contain a cytosine triphosphate deoxynucleotide ("C") followed by a guanine triphosphate deoxynucleotide ("G"). The "p" refers to the phosphodiester link between consecutive nucleotides, although some ODN have a modified phosphorothioate (PS) backbone instead. When these CpG motifs are unmethylated, they act as immunostimulants CpG motifs are considered pathogen-associated molecular patterns (PAMPS) due to their abundance in microbial genomes but their rarity in vertebrate genomes. The CpG PAMP is recognized by the pattern recognition receptor (PRR) Toll-Like Receptor 9 (TLR9), which is constitutively expressed only B cells and plasmacytoid dendritic cells (pDCs) in humans and other higher primates.

CSC Vaccines

The optimized CSC vaccine of the present invention combines several novel components to create a vaccine capable of inducing effective anti-tumor immunity, against a variety of different tumor types. In certain embodiments, preparation of the CSC vaccine utilizes a tumor cell line derived from the type of tumor to be vaccinated against (e.g., a breast cancer cell line to prepare breast CSC vaccine), but it does not require that the tumor cell line be obtained from or matched to the patient. However, in some particular embodiments, the CSC vaccine is prepared from a tumor cell line derived from tumor cells obtained from the patient to whom the CSC vaccine is intended to be administered, or the CSC vaccine is prepared from a tumor cell line matched to the patient. In other particular embodiments, the CSC vaccine is prepared from tumor cells that are completely unrelated (allogeneic) to the patient, i.e., not the patient's own tumor cells. In particular embodiments, the tumor cell line used is the same species as the patient, but fully allogeneic.

In particular embodiments, the CSC vaccines comprise or consist of the following components:

1. CSC antigens, e.g., CSC antigens prepared from tumor cells grown in vitro under conditions that promote the growth of tumor cells that acquire features characteristic of CSCs;

2. one or more vaccine adjuvants, e.g., cationic liposome-DNA complexes (CLDC adjuvant) or cationic liposome DNA-pIC complexes (CLDPC), either with or without a cellular adhesion agent (e.g., carboxymethyl cellulose or PEG); and 3. optionally, an agent that increases or amplifies cellular immunity (i.e., a vaccine enhancing agent).

In particular embodiments, the CSC vaccines comprise all three of these components. In certain embodiments, two or more, or three or more of the components of the CSC vaccine are present in the same pharmaceutical composition, which may further comprise one or more excipients, diluents or carriers. The pharmaceutical compositions may be sterile.

In particular embodiments, the agent that increases or amplifies cellular immunity is present in the same pharmaceutical composition as the vaccine adjuvant or is incorporated into the vaccine adjuvant. In certain embodiments, the one or more vaccine adjuvant comprises a CDLC adjuvant or a CLDPC adjuvant. In certain embodiments, the one or more vaccine adjuvant further comprises a cellular adhesion agent, e.g., carboxymethyl cellulose or PEG.

In certain embodiments, the CSC vaccines comprise or consist of the following components:

1. CSC antigens prepared from tumor cells grown in vitro under conditions designed specifically to promote the growth of tumor cells that acquire features characteristic of true CSC;

2. a vaccine adjuvant consisting of cationic liposome-DNA complexes (CLDC adjuvant) or cationic liposome DNA-pIC complexes (CLDPC); and 3. a CCR2 antagonist drug incorporated into vaccine adjuvant to amplify cellular immunity. In certain embodiments, the CCR2 antagonist drug may be substituted any drug that functionally exerts the same effect as a CCR2 antagonist drug, e.g., any drug that blocks monocyte migration to a chemokine gradient.

In certain embodiments, any of the CSC vaccines described herein further comprises a non-specific cellular adhesion agent, such as carboxymethyl cellulose. In certain embodiments, the CCR2 antagonist drug may be substituted any drug that functionally exerts the same effect as a CCR2 antagonist drug, e.g., any drug that blocks monocyte migration to a chemokine gradient.

Preparation of CSCs and CSC Antigens

In particular embodiments, CSC vaccines include in vitro derived CSC antigens, e.g., CSC antigens prepared as described herein. In certain embodiments of preparing CSC antigens, tumor cell lines are placed in cell culture conditions designed to specifically induce the generation of CSC in vitro. Under normal tissue culture conditions, CSCs are very rare in tumor cell lines. In particular embodiments, tumor cell lines are cultured under conditions to generate more immunogenic CSC capable of eliciting strong immunity against CSC in patients or animals with cancer.

CSCs, CSC antigens, and CSC vaccines may be produced from a variety of different tumor cells, including primary tumor cells and tumor cell lines. Primary tumor cells may be obtained directly from a tumor obtained from an animal and purified by any of several different techniques, including most often flow cytometric cell sorting. Tumor cell lines may be early passage tumor cell lines, or they may be immortalized tumor cell lines. Tumor cells may be any type of tumor, including but not limited to, breast cancer, lung cancer, prostate cancer, colorectal cancer (e.g., colon carcinoma), brain cancer, esophageal cancer, stomach cancer, bladder cancer, pancreatic cancer, cervical cancer, head and neck cancer, ovarian cancer, melanoma, leukemia, myeloma, lymphoma, glioma, Non-Hodgkin's lymphoma, leukemia, multiple myeloma and multidrug resistant cancer.

The present invention includes methods of culturing a tumor cell lines to increase or enhance the generation of CSCs, comprising culturing the tumor cell lines under conditions and for a time sufficient to generate CSCs. In particular embodiments, a cultured tumor cell line resulting from this method includes at least 25% more, at least 50% more, at least 2-fold greater, at least 5-fold greater, or at least a 10-fold greater CSCs as compared to the tumor cell line when cultured under standard conditions. In this description, "standard" tumor culture conditions refer to culture in any cell culture medium (e.g., DME or MEME) supplemented with fetal bovine serum (FBS), typically in 10% v/v FBS.

CSCs may be identified by the expression of cell surface markers specific for stem cells, such as, e.g., CD90, CD117, Sca1, CD133, CD34, CD73, Nanog, Klf-4, and Oct3/4. Other markers include ALDH (aldehyde dehydrogenase) expression. Functional stem cell assays also include side-scatter populations (e.g., Hoechst dye exclusion). Marker expression may be determined and measured by any means available in the art, including, e.g., fluorescence activated cell sorting methods using labeled antibodies that specifically bind to the markers, or use of membrane permeable dyes such as Hoechst dye.

In one embodiment, the tumor cells lines and CSCs are grown in serum-free medium, under non-adherent conditions, with one or more growth factors, such as, e.g., one or more growth factors selected from: an epidermal growth factor (EGF), basic fibroblast growth factor (FGF), insulin, insulin-like growth factor (IGF), Notch ligand (e.g., frizzled), Wnt ligand, or certain chemokines (eg, IL-8) and growth factors (e.g., G-CSF). Typical growth factor or chemokine concentrations include 1 ng/ml to 100 ng/ml. In particular embodiments, the growth factor is EGF and/or bFGF. Cells are typically cultured for between 7 and 40 days (most desirable 30 days) before the cells are harvested for preparation of the stem cell antigens.

In another embodiment, tumor cells lines and CSCs are cultured in serum-free basal medium supplemented with insulin-selenium-transferrin mixture (B27 supplement, prepared by manufacturer, and used at between 10% and 50% v/v with defined cell culture medium (either DME or DME-F12 medium) supplemented with at minimum EGF (10 ng/ml) and bFGF (10 ng/ml). In certain embodiments, the one or more growth factors are selected from: an epidermal growth factor (EGF), fibroblast growth factor (FGF), G-CSF, Notch ligand, and Wnt ligand. In certain embodiments, the growth factor(s) include bFGF and EGF. In certain embodiments, the growth factors include about 10 ng/ml basic fibroblast growth factor (bFGF) and about 10 ng/ml epidermal growth factor (EGF). In particular embodiments, the cells are cultured on non-stick, Teflon-coated tissue culture plates.

The present invention further includes methods of preparing CSC antigens, comprising culturing tumor cells under conditions described herein to increase or enhance production of CSCs, and then processing the cells to release CSC antigens. In particular embodiments, the cells cultured under stem cell enrichment conditions are then lysed by freeze-thaw and sonication to release CSC antigens into solution. The proteins and cell membrane materials released from the lysed CSC cultures are then included in the CSC vaccine. In one illustrative method of preparing antigens for the CSC vaccine, the CSC are subjected to 3 freeze-thaw cycles to lyse the cells and release antigens into solution. These antigens may then incorporated into the CSC vaccine. In certain embodiments, an antigen dose of 50 to 100 ug protein per vaccine is used, as determined by BCA assay. In particular embodiments, this antigen dose is the amount of total protein in the CSC lysate.

The present invention also includes CSCs, e.g., a plurality of CSCs, including CSCs prepared according to any of the methods described herein. In particular embodiments, the CSCs are produced from or derived from tumor cells, including any of the tumor cell types described herein. In particular embodiments, the CSCs have increased expression of one or more of CD90, CD117, Sca1, CD133, CD34, CD73, Nanog, Klf-4, Oct3/4, and ALDH (aldehyde dehydrogenase) as compared to the tumor cells from which the CSCs were produced or derived. In particular embodiments, the increased expression is at least 1.1-fold, at least 1.2-fold, at least 1.5-fold, at least 2-fold, at least 5-fold, or at least 10-fold greater.

The present invention also includes a composition comprising CSC antigens, e.g., a plurality of CSC antigens, including CSC antigens prepared according to any of the methods described herein. In particular embodiments, the CSC antigens are produced from or derived from CSCs generated from or derived from tumor cells, including any of the tumor cell types described herein. In particular embodiments, the CSCs have increased expression of one or more of CD90, CD117, Sca1, CD133, CD34, CD73, Nanog, Klf-4, Oct3/4, and ALDH (aldehyde dehydrogenase) as compared to the tumor cells from which the CSCs were produced or derived. In particular embodiments, the increased expression is at least 1.1-fold, at least 1.2-fold, at least 1.5-fold, at least 2-fold, at least 5-fold, or at least 10-fold greater. In particular embodiments, the composition comprising CSC antigens is a pharmaceutical composition and further comprises one or more pharmaceutically acceptable carriers, diluents, or excipients.

Vaccine Adjuvants

The CSC vaccine also includes one or more vaccine adjuvant. In one embodiment, the vaccine adjuvant for the CSC vaccine is a cationic liposome combined with a TLR9 agonist (either plasmid DNA (e.g., non-coding plasmid DNA), or CpG oligos), known as a CLDC adjuvant. In one embodiment, the vaccine adjuvant for the CSC vaccine is a cationic liposome combined with a TLR9 agonist and a TLR3 agonist. In one embodiment, the vaccine adjuvant for the CSC vaccine is a cationic liposome DNA-pIC complex (CLDPC). In certain embodiments, the vaccine adjuvant comprises cationic liposomes, a mixture of toll like receptor 3 (TLR3) and toll like receptor 9 (TLR9) ligands, and, optionally, a cellular adhesion agent. In particular embodiments, the adjuvant is immunostimulatory.

In particular embodiments of the adjuvant, the cationic liposomes comprise a cationic lipid, optionally DOTAP. In certain embodiments, the cationic liposomes comprise cholesterol. In certain embodiments, the cationic liposomes comprise the cationic lipid, optionally DOTAP, and cholesterol in a 2:1 to 1:3 molar ratio. In certain embodiments, the cationic liposomes comprise the cationic lipid, optionally DOTAP, and cholesterol in an about 1:2 molar ratio.

In particular embodiments of the adjuvant, the mixture of TLR3 and TLR9 ligands comprises plasmid DNA and/or polyI:C. In certain embodiments, the mixture comprises plasmid DNA and polyI:C. In certain embodiments, the mixture comprises plasmid DNA and polyI:C in a 2:1 to 1:2 ratio (by weight). In certain embodiments, the mixture comprises plasmid DNA and polyI:C in an about 1:1 ratio (by weight).

In particular embodiments of the adjuvant, the cellular adhesion agent is a carboxy methylcellulose or a PEG. In certain embodiments the cellular adhesion agent is a low- to mid-weight viscosity carboxy methylcellulose. In certain embodiments, the carboxy methylcellulose is present at about 1% to 20% (v/v). In certain embodiments, the carboxy methylcellulose is present at about 5% (v/v).

In particular embodiments of the adjuvant, the adjuvant comprises complexes of the cationic liposomes and the TLR3 and TLR9 ligands (TLR ligands). In certain embodiments, the complexes comprise about 10 ug to about 500 ug of the TLR ligands per 1 ml of the cationic liposomes. In certain embodiments, the complexes comprise about 100 ug of the TLR ligands per 1 ml of the cationic liposomes.

The CSC vaccines may elicit both a cell-mediated immune response and a humoral immune response. In certain embodiments, this immune response will induce long lasting antibodies plus a T cell-mediated immune response, which could involve CD4 or CD8 T cells, or both. The CLDC adjuvant primarily elicits a Th1 response to CSC antigens present in the CSC vaccine. In particular embodiments, the CSC vaccine is prepared by mixing CSC antigens with CLDC adjuvant and/or CLDPC adjuvant capable of eliciting effective cell-mediated immunity. In certain embodiments, the adjuvants may include other adjuvants capable of eliciting Th1 immune responses.

In certain embodiments, the vaccine contains a cellular adhesion agent, which may enhance uptake of the vaccine or antigen thereof. In particular embodiments, the vaccine contains both a CLDC adjuvant and a cellular adhesion agent. In particular embodiments, the vaccine contains both a CLDPC adjuvant and a cellular adhesion agent.

In particular embodiments, the cellular adhesion agent is carboxymethyl cellulose, e.g. a low to mid-weight viscosity formulation. Carboxymethyl cellulose (CMC) or cellulose gum is a cellulose derivative with carboxymethyl groups (—CH$_2$—COOH) bound to some of the hydroxyl groups of the glucopyranose monomers that make up the cellulose backbone. It is often used as its sodium salt, sodium carboxymethyl cellulose. In particular embodiments, CMC is present in the vaccine at 1% to 20% (v/v), 2% to 15%, 2.4% to 10%, or about 5% (v/v). In particular embodiments of low viscosity carboxymethylcellulose (CMC), the viscosity of a 4% solution in water at 25° C. is 50-200 centipoise (cps). The viscosity is both concentration and temperature dependent. As the temperature increases, the viscosity decreases. As the concentration increases, the viscosity increases. In various embodiments, low, medium and high viscosity carboxymethylcellulose (CMC) are used in the CSC vaccines of the present invention. Low viscosity CMC is usually used in "thin" aqueous solutions. Medium viscosity CMC is usually used to make solutions that look like a syrup. In particular embodiments, low viscosity CMC has a molecular weight of about 90 kDa; a degree of polymerization of 400; a degree of substitution of 0.65-0.90 (6.5-9.0 carboxymethyl groups per 10 anhydroglucose units); and a sodium content of about 8% by weight. In particular embodiments, medium viscosity carboxymethylcellulose (CMC) has a viscosity of a 2% solution in water at 25° C. of 400-800 centipoise (cps). The viscosity is both concentration and temperature dependent. As the temperature increases, the viscosity decreases. As the concentration increases, the viscosity increases. In particular embodiments, medium viscosity CMC has a molecular weight of about 250 kDa; a degree of polymerization of about 1100; and a degree of substitution of about 0.7 (approximately 7 carboxymethyl groups per 10 anhydroglucose units). In particular embodiments, high viscosity carboxymethylcellulose (CMC) has a viscosity of a 1% solution in water at 25° C. is 1500-3000 centipoise (cps). The viscosity is both concentration and temperature dependent. As the temperature increases, the viscosity decreases. As the concentration increases, the viscosity increases. In particular embodiments, high viscosity CMC is used to make a mixture that resembles a cream or lotion. In certain embodiments, low viscosity CMC is used in "thin" aqueous solutions. In particular embodiments, high viscosity CMC has a molecular weight of about 700 kDa; a degree of polymerization of 3200; and a degree of substitution of about 0.65-0.85 (6.5-8.5 carboxymethyl groups per 10 anhydroglucose units). As used herein, a "poise" is a unit of viscosity based on a flow rate using the standard of water @ 20° C. having a poise value of exactly 1 centipoise or one hundredth of a poise. One poise may be defined as "P" in the following equation: $1P=(0.10 \text{ kg/meter})/\text{sec}=(1 \text{ g/cm})/\text{sec}$.

In certain embodiments, the cellular adhesion agent is a polyethylene glycol. As used herein, "Polyethylene glycol" or "PEG" is a polyether compound of general formula H—(O—CH2-CH2)n-OH. PEGs are also known as polyethylene oxides (PEOs) or polyoxyethylenes (POEs), depending on their molecular weight PEO, PEE, or POG, as used herein, refers to an oligomer or polymer of ethylene oxide. The three names are chemically synonymous, but PEG has tended to refer to oligomers and polymers with a molecular mass below 20,000 g/mol, PEO to polymers with a molecular mass above 20,000 g/mol, and POE to a polymer of any molecular mass. PEG and PEO are liquids or low-melting solids, depending on their molecular weights. Throughout this disclosure, the 3 names are used indistinguishably. PEGs are prepared by polymerization of ethylene oxide and are commercially available over a wide range of molecular weights from 300 g/mol to 10,000,000 g/mol. In certain embodiments, the PEG is water-soluble (amphiphilic or hydrophilic), non-toxic, and pharmaceutically inert. Suitable polymeric moieties include polyethylene glycols (PEG), homo- or co-polymers of PEG, a monomethyl-substituted polymer of PEG (mPEG), or polyoxyethylene glycerol (POG). See, for example, Int. J. Hematology 68:1 (1998); Bioconjugate Chem. 6:150 (1995); and Crit. Rev. Therap. Drug Carrier Sys. 9:249 (1992). Suitable PEG polymers will vary substantially by weights ranging from about 200 to about 60,000. In certain embodiments, PEGs having molecular weights from 200 to 2,000 or from 200 to 500 are used. Lower-molecular-weight PEGs are also available as pure oligomers, referred to as monodisperse, uniform, or discrete. These are used in certain embodiments of the present invention. PEGs are also available with different geometries: branched PEGs have three to ten PEG chains emanating from a central core group; star PEGs have 10 to 100 PEG chains emanating from a central core group; and comb PEGs have multiple PEG chains normally grafted onto a polymer backbone. PEGs can also be linear.

In certain embodiments, the CLDC adjuvant comprises: cationic liposomes (e.g., DOTAP and cholesterol, 1:2 to 2:1 ratio or about 1:1 ratio), and non-coding plasmid DNA (10 ug/ml to 500 ug/ml or 10 ug/ml to 200 ug/ml, or about 50 ug/ml). In particular embodiments, the CLDC adjuvant comprises cationic liposomes (e.g., DOTAP and cholesterol, 1:1 ratio), and non-coding plasmid DNA (50 ug/ml). In particular embodiments, a CSC vaccine includes both a CLDC adjuvant and carboxymethyl cellulose (CMC) at 1% to 20%, 2% to 15%, 2.5% to 10%, 5% or 10% or about 5% v/v with the final vaccine.

In certain embodiments, the CLPDC adjuvant comprises: cationic liposomes (e.g., DOTAP and cholesterol, 1:2 to 2:1 ratio or about 1:1 ratio), non-coding plasmid DNA (10 ug/ml to 500 ug/ml or 10 ug/ml to 200 ug/ml, or about 50 ug/ml), and synthetic pIC (10-500 ug/ml or 10-200 ug/ml or about 50 ug/ml). In particular embodiments, the LPDC adjuvant comprises cationic liposomes (e.g., DOTAP and cholesterol, 1:1 ratio), non-coding plasmid DNA (50 ug/ml), and synthetic pIC (50 ug/ml). In particular embodiments, a CSC vaccine includes both a CLPDC adjuvant and carboxymethyl cellulose (CMC) at 1% to 20%, 2% to 15%, 2.5% to 10%, 5% or 10% or about 5% v/v with the final vaccine.

In one embodiment, the CSC vaccine may be prepared by preparing complexes of cationic liposomes with DNA and pIC, then adding the vaccine antigen. The CMC adhesive agent (also referred to as the cellular adhesive agent) is then added to the combined complexes and vaccine antigen. In particular embodiments, the CSC vaccine is administered subcutaneously or intramuscularly.

Two types of T cells, CD4 and CD8 cells, initiate and/or enhance cell mediated immunity and humoral immunity. CD8 T cells interact with antigens displayed on MHC Class I molecules. CD4 T cells recognize antigenic peptides bound to MEW class II molecules. Upon interaction with a MHC class II molecule, the CD4 cells secrete factors such as cytokines, which activate B cells, cytotoxic T cells, macrophages, and other cells that participate in an immune response. Helper T cells or CD4+ cells can be further divided into two functionally distinct subsets: TH1 phenotype and TH2 phenotypes which differ in their cytokine and effector function. Activated TH1 cells enhance cellular immunity (including an increase in antigen-specific CTL production) and are therefore of particular value in responding to intracellular infections. Activated TH1 cells may secrete one or more of IL-2, IFN-gamma, and TNF-beta. A TH1 immune response may result in local inflammatory reactions by activating macrophages, NK (natural killer) cells, and CD8 cytotoxic T cells (CTLs). Activated TH2 cells enhance antibody production. Activated TH2 cells may secrete one or more of IL-4, IL-5, IL-6, and IL-10. A TH2 immune response may result in the production of IgG1, IgE, IgA and memory B cells for future protection. An enhanced immune response may include one or more of an enhanced TH1 immune response and a TH2 immune response. A TH1 immune response may include one or more of an increase in CTLs, an increase in one or more of the cytokines associated with a TH1 immune response (such as IL-2, IFN-gamma, and TNF-beta), an increase in activated macrophages, an increase in NK activity, or an increase in the production of IgG2a. In some embodiments, the enhanced TH1 immune response will include an increase in IgG2a production. A TH1 immune response may be elicited using a TH1 adjuvant. A TH1 adjuvant will generally elicit increased levels of IgG2a production relative to immunization of the antigen without adjuvant. TH1 adjuvants suitable for use in the invention may include for example saponin formulations, virosomes and virus like particles, non-toxic derivatives of enterobacterial lipopolysaccharide (LPS), immunostimulatory oligonucleotides. Immunostimulatory oligonucleotides, such as oligonucleotides containing a CpG motif, are typical TH1 adjuvants for use in the invention.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. In some embodiments, the enhanced TH2 immune response will include an increase in IgG1 production. A TH2 immune response may be elicited using a TH2 adjuvant. A TH2 adjuvant will generally elicit increased levels of IgG1 production relative to immunization of the antigen without adjuvant. TH2 adjuvants suitable for use in the invention include, for example, mineral containing compositions, oil-emulsions, and ADP-ribosylating toxins and detoxified derivatives thereof. Mineral containing compositions, such as aluminium salts are typical TH2 adjuvants for use in the invention.

The vaccine adjuvant may be any adjuvant known or used in the art, including but not limited to: CLDC adjuvants, mineral salts, such as aluminium salts and calcium salts, including hydroxides (e.g., oxyhydroxides), phosphates (e.g., hydroxyphosphates, orthophosphates) and sulphates, etc.; oil-in-water emulsions, such as squalene-water emulsions, including MF59 (5% Squalene, 0.5% Tween 80, and 0.5% Span 85, formulated into submicron particles using a microfluidizer); complete Freund's adjuvant (CFA) and incomplete Freund's adjuvant (IFA); saponin formulations, such as QS21 and ISCOMs; virosomes and virus-like particles (VLPs); bacterial or microbial derivatives, such as non-toxic derivatives of enterobacterial lipopolysaccharide (LPS), Lipid A derivatives; immunostimulatory oligonucleotides, such as IC-31 (deoxynucleotide comprising 26-mer sequence 5'-(IC)$_{13}$-3' and polycationic polymer polypeptide comprising 11-mer amino acid sequence KLKLLLLLKLK) and ADP-ribosylating toxins and detoxified derivatives thereof; human immunomodulators, including cytokines, such as interleukins (e.g., IL-1, IL-2, IL-4, IL-5, IL-6, IL-7, IL-12, interferons (e.g., interferon-gamma), macrophage colony stimulating factor, and tumor necrosis factor; bioadhesives and mucoadhesives, such as chitosan and derivatives thereof, esterified hyaluronic acid microspheres or mucoadhesives, such as cross-linked derivatives of poly(acrylic acid), polyvinyl alcohol, polyvinyl pyrollidone, polysaccharides and carboxymethylcellulose; microparticles (e.g., a particle of about 100 nm to about 150 um in diameter) formed from materials that are biodegradable and non-toxic (e.g., a poly(alpha-hydroxy acid), a polyhydroxybutyric acid, a polyorthoester, a polyanhydride, a polycaprolactone, etc.); liposomes; polyoxyethylene ethers and polyoxyethylene esters; PCPP formulations; muramyl polypeptides, including N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-s-n-glycero-3-hydroxyphosphoryloxy)-ethylamine MTP-PE); and imidazoquinolone compounds, including Imiquamod and its homologues (e.g. "Resiquimod 3M"). Illustrative adjuvants suitable for use include, but are not limited to, cationic lipid DNA complexes (CLDC), cationic lipid DNA pI:C complexes (CLDPC), CpG-oligonucleotides, poly I:C, LPS, alpha-galactosylceramide, and the like.

In particular embodiments, the adjuvant will comprise or consist of cationic liposomes complexed to non-coding plasmid DNA (CLDC), as this adjuvant is particularly effective in eliciting T cell (both CD8 and CD4) responses to protein antigens. The CLDC adjuvant can also be prepared using cationic liposomes admixed with CpG oligos. In particular embodiments, the CLPDC includes cationic liposomes complexed to polyI:C and plasmid DNA. In certain embodiments, the complex includes cationic liposomes (e.g., DOTAP) in a 1:1 to 1:2 molar ratio with cholesterol, e.g., formulated as small unilamellar vesicles in dextrose or sucrose solution, and polyI:C and/or plasmid DNA (e.g., non-coding DNA). When both are present, in certain embodiments, the polyI:C and plasmid DNA may be present in a ratio of 1:2 to 2:1, e.g., 1:1 (by weight). In certain embodiments, the complex contains about 10 ug to about 500 ug, about 50 ug to about 200 ug or about 100 ug total of pIC and/or DNA per 1 ml liposomes. In other embodiment, the cationic liposomes are comprised of a cationic lipid (e.g., DOTAP or DOTIM) mixed with a 1:1 molar ratio of cholesterol and rehydrated to produce liposomes in the range of 250 nm diameter, see, e.g., Dow, S. W. et al., J Immunol, 1999, 163:1552-1561; Zaks, K. et al., J Immunol, 2006, 176:7335-7345; Mitchell, L. A. et al., J. Immunology, 2012, 189; and Dow et al., Liposome Adjuvant Review, 2007). In particular embodiments, any of the CLDC and CLPDC adjuvants also include a cellular adhesive agent, such as carboxymethyl cellulose. The present invention includes any adjuvant described in any of these references.

Agents that Increase or Amplify Cellular Immunity

In certain embodiments, the CSC vaccine also contains a vaccine enhancing agent (VEA), which increases or enhances the cellular and humoral immune response to the CSC antigens present in the vaccine. Potential VEAs include specific CCR2 antagonists (e.g., RS102895), or other drugs that block monocyte migration (e.g., losartan, telmisartan, irbesartan), ondansetron, or drugs that otherwise interfere with monocyte maturation or function (eg, MCSF-receptor antagonists, sildenafil, and certain antibiotics (e.g., norfloxacin). In certain embodiments, the VEA is an inhibitor of monocyte migration, e.g., a monocyte migration inhibiting drug that acts through another pathway, instead of, or in addition to, the CCR2 pathway. Examples of such inhibitors include, but are not limited to angiotensin receptor blocking (ARB) drugs, as well as compounds of any of Formula (I)-(V), such as ondansetron. In other examples, the VEA is losartan, incorporated at a dose of 250 ug directly with the vaccine. In another example, the VEA is ondansetron incorporated at a dose of 250 ug directly with vaccine.

CCR2 Antagonists

In certain embodiments, the VEA is a CCR2 antagonist drug, e.g., which may block recruitment of inflammatory CCR2+ monocytes, and which may optionally be incorporated directly with the vaccine adjuvant. The major chemokine regulating monocyte recruitment is MCP-1 (CCL2), which signals primarily via activation of the receptor CCR2 expressed principally on inflammatory monocytes. Several specific small molecule inhibitors of CCR2 have been developed for treatment of inflammatory diseases such as rheumatoid arthritis, asthma, and atherosclerosis. For example, in certain embodiments, the CCR2 antagonist is the small molecule drug RS102895. In certain embodiments, about 250 ug of RS102895 is incorporated into a 1 ml vaccine, e.g., along with 100 ug of CLDC adjuvant and 100 ug of CSC antigen. In particular embodiments, a CRC vaccine comprises CRC antigens, a vaccine adjuvant, and a CCR2 antagonist.

The Examples herein demonstrate the use of an illustrative small molecule CCR2 inhibitor; however, it is explicitly considered that virtually any CCR2 inhibitor and/or antagonist is suitable for use according to the present disclosure. In particular embodiments, the CCR2 antagonist inhibits monocyte migration. CCR2 antagonists that may be used in CRC vaccines of the present include, but are not limited to, those described in US patent application publication US 2012/0156280, U.S. Pat. No. 8,975,290 and PCT Publication No. WO2014/134621, each of which is incorporated herein by reference in its entirety. Other CCR2 antagonist that may be used include those described in Higgins et al. (2007) (Chemokine Biology-Basic Research and Clinical Application, Vol. II, Birkhauser Verlag Basel Switzerland, pg. 115-123) and Mirzadegan et al. (2000) (The Journal of Biological Chemistry, Vol. 275, No. 33, August, pg. 25562-25571), which are hereby incorporated by reference in their entireties. While not intending to be limited in any way by this exemplary set of CCR2 molecules, Table 1 presents a number of CCR2 antagonists that are considered to be suitable for use according to the present invention.

TABLE 1

| Company | CCR2 antagonists |
|---|---|
| Roche/Iconix | 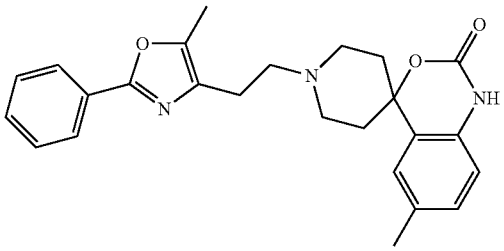<br>CCR2 IC(50) - 89 nM bind, 210 nM taxis |
| Millenium/Pfizer | 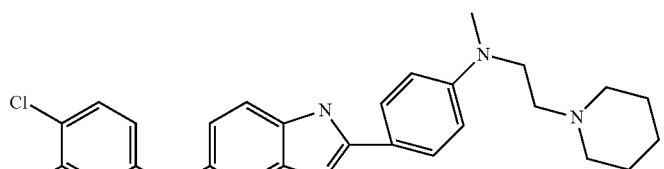<br>Benzimidazoles<br>CCR IC(50) - 200-300 nM bind |

TABLE 1-continued
| Company | CCR2 antagonists |
|---|---|
| SmithKline | 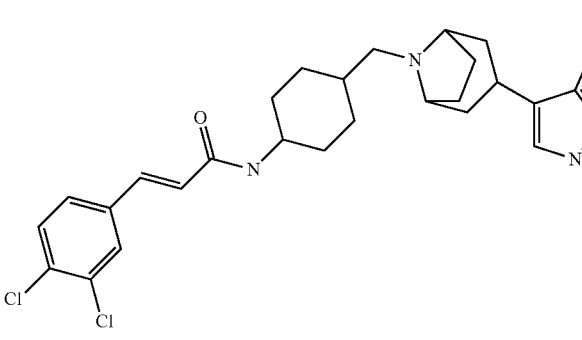<br>SB-380732<br>50 nM bind |
| AstraZeneen | AZD-6942<br>29 nM bind; 60 nM taxis |
| Merck | 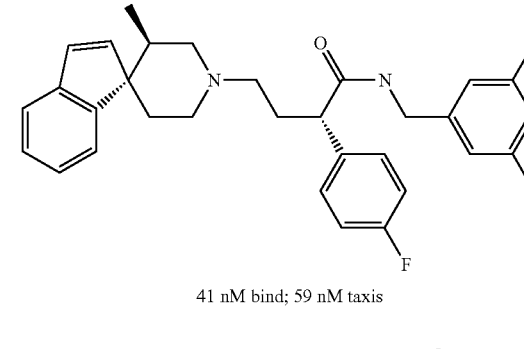<br>41 nM bind; 59 nM taxis |
| Teija/BMS | 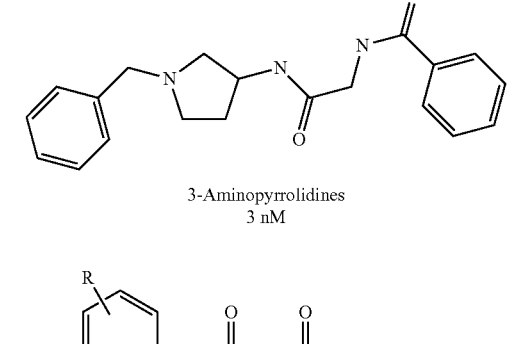<br>3-Aminopyrrolidines<br>3 nM |
| Telik | 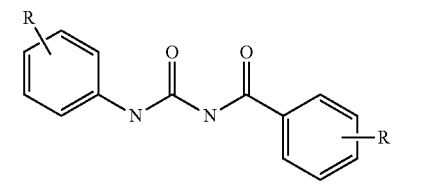 |
| Incyte | 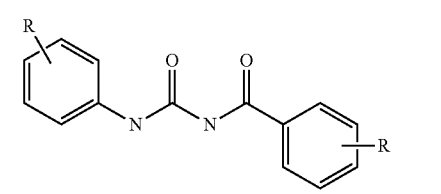<br>INCB-003284 |
| Tocris | RS 102895 hydrochloride (Catalog #2089) |

TABLE 1-continued

| Company | CCR2 antagonists |
|---|---|
| Biosciences | 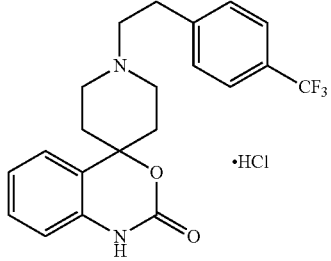<br>IC$_{50}$ values are 0.36 and 17.8 µM for inhibition of human recombinant CCR2b and CCR1 receptors respectively. Blocks MCP-1-stimulated calcium influx and chemotaxis with IC$_{50}$ values of 32 nM and 1.7 µM respectively. Also inhibits $\alpha_{1A}$; $\alpha_{1D}$ and 5-HT$_{1A}$ receptors. |

In addition, many other CCR2 inhibitors and/or CCR2 antagonists in development (e.g., but not limited to, RS-21825, RS-29634, and RS-136270, disclosed in Mirzadegan et al. and PF-0417890) are considered to be suitable for use according to the present disclosure. Particular compounds of interest from the list above are RS102895 (Tocris, Catalog number 2089) and RS504393 (Roche/Iconix).

Angiotensin II Receptor Blockers (ARBs)

In certain embodiment, the VEA is an Angiotensin II receptor blocker or "ARB" (also known as angiotensin receptor antagonists, AT$_1$-receptor antagonists, or sartans). In particular embodiments, a CRC vaccine comprises CRC antigens, a vaccine adjuvant, and an ARB.

ARBs are a group of pharmaceuticals which modulate the renin-angiotensin-aldosterone system by selectively inhibiting the effects of angiotensin II (Ang II), a peptide hormone that plays an important role in the pathophysiology of hypertension. ARBs antagonize the action of Ang II at the Ang II type 1 (AT$_1$) receptor and produce their blood pressure lowering effects by reversing the effects of Ang II, including, e.g., vasoconstriction, aldosterone release, ADH secretion, ACTH secretion, increased sodium absorption by the kidney, and catecholamine release. Losartan was the first ARB to be developed and approved by the United States Food and Drug Administration (FDA), and it has served as the basis for the development of other ARBs, including Azilsartan, Candesartan, Eprosartan, Irbesartan, Olmesartan, Telmisartan, and Valsartan, each of which is also approved by the FDA for clinical use. Each of the ARBs described above is known by a number of trade names, the most common of which are listed in Table 2 below.

TABLE 2

ARBs and Trade Names

| Drug | Trade Names |
|---|---|
| Azilsartan | Edarbi ® |
| Candesartan | Blopress ®, Atacand ® |
| Eprosartan | Teveten ® |
| Irbesartan | Avapro ® |
| Losartan | Cozaar ®, Anzar ®, Arbloc ®, Angisartan ® Hartzar ®, Pharex ®, Neosartan ®, Hyoerthree ®, Getzar ®, Kenzar ®, Lozaris ®, Qxar ®, Normoten ®, Ecozar ®, Lifezar ® |
| Olmesartan | Olmezar ®, Olmetec ® |
| Telmisartan | Micardis ®, Pritor ®, Benicar ® |
| Valsartan | Diovan ® |

In certain embodiments, methods described herein comprise administering an ARB, and compositions and kits described herein comprise an ARB. In certain embodiments, compositions and kits of the invention include any ARB, any combination of ARBs, or any prodrug, salt, or derivative of any ARB shown in Table 2.

Accordingly, in certain embodiments, the compositions of the invention include Losartan, e.g., where the Losartan in the composition (e.g., a typical 1 ml vaccine) is at a concentration sufficient to provide a dose of at least about 5 mg, at least about 10 mg, at least about 15 mg, at least about 20 mg, at least about 25 mg, at least about 30 mg, at least about 35 mg, at least about 40 mg, at least about 45 mg, at least about 50 mg, at least about 60 mg, at least about 70 mg, at least about 80 mg, of Losartan, including any range in between these values, or less than about 50 mg, or less than about 25 mg of Losartan, including any range in between these values. In certain embodiments, the Losartan in the composition is at a concentration sufficient to provide a dose of more than about 80 mg, more than about 100 mg, more than about 125 mg, more than about 150 mg, more than about 175 mg, or more than about 200 mg or Losartan, including any range in between about 5 mg and about 200 mg.

In certain embodiments, compositions of the invention can include Losartan at a concentration sufficient to provide a dose of at least about 0.5 mg/kg, at least about 0.75 mg/kg, at least about 1.0 mg/kg, at least about 1.25 mg·kg, at least about 1.5 mg/kg, at least about 1.75 mg/kg, or at least about 2.0 mg/kg of Losartan, including any range between about 0.5 mg/kg and about 1.75 mg/kg. In certain embodiments, compositions of the invention can include Losartan at a concentration sufficient to provide a dose of more than about 1.75 mg/kg, at least about 2.0 mg/kg, at least about 5 mg/kg, at least about 7 mg/kg, at least about 10 mg/kg, at least about 12 mg/kg, at least about 15 mg/kg, at least about 17 mg/kg, at least about 20 mg/kg, at least about 22 mg/kg, at least about 25 mg/kg, at least about 27 mg/kg, or at least about 30 mg/kg or Losartan, including any range in between about 1.75 mg/kg and about 30 mg/kg. In certain embodiments, the compositions of the invention can include Losartan at a concentration sufficient to provide a dose of more than about 30 mg/kg, e.g., at least about 35 mg/kg or at least about 40 mg/kg of Losartan, including any range in between about 30 mg/kg and about 40 mg/kg.

In certain embodiments, the invention provides compositions that can include Azilsartan and an antigen, vaccine, or anti-tumor preparation, where the Azilsartan, e.g., at a concentration sufficient to provide a dose of at least about 10 mg, at least about 20 mg, at least about 40 mg, at least about 60 mg, at least about 70 mg, at least about 80 mg, of Azilsartan, including any range in between these values, or less than about 50 mg, or less than about 80 mg, including any range between these values. In certain embodiments, the Azilsartan in the composition is at a concentration sufficient to provide a dose of more than about 80 mg, more than about 100 mg, more than about 120 mg, more than about 140 mg, or more than about 160 mg, including any range in between these values.

In certain embodiments, the invention also provides compositions that can include Candesartan, e.g., where the Candesartan in the composition is at a concentration sufficient to provide a dose of at least about 0.5 mg, at least about 1 mg, at least about 2 mg, at least about 3 mg, or less than about 4 mg, including any range between these values. In certain embodiments, the Candesartan in the composition is at a concentration sufficient to provide a dose of more than about 32 mg, more than about 40 mg, more than about 48 mg, more than about 56 mg, more than about 64 mg or more than about 84 mg, including any range in between these values. In certain embodiments, the Candesartan in the composition is at a concentration sufficient to provide a dose of less than about 32 mg, less than about 40 mg, less than about 48 mg, less than about 56 mg, less than about 64 mg or less than about 84 mg, including any range in between these values.

In certain embodiments, certain compositions of the invention can include Eprosartan, e.g., where the Eprosartan in the composition is at a concentration sufficient to provide a dose of at least about 50 mg, at least about 100 mg, at least about 200 mg, at least about 300 mg, at least about 400 mg, at least about 500 mg, at least about 600 mg, at least about 700 mg, at least about 800 mg, including any range between these values, or less than about 400 mg, less than about 300 mg, less than about 200 mg, or less than about 100 mg, including any range between these values. In certain embodiments, the Eprosartan in the composition is at a concentration sufficient to provide a dose of more than about 600 mg, more than about 750 mg, more than about 900 mg, more than about 1050 mg, or more than about 1200 mg, including any range in between these values.

In certain embodiments compositions of the invention can include Irbesartan, e.g., where the Irbesartan in the composition is at a concentration sufficient to provide a dose of at least about 12.5 mg, at least about 25 mg, at least about 50 mg, at least about 75 mg, at least about 100 mg, at least about 125 mg, at least about 150 mg, at least about 175 mg, at least about 200 mg, at least about 250 mg, at least about 275 mg, or at least about 300 mg, including any range between these values, or less than about 150 mg, less than about 100 mg, less than about 50 mg, including any range between these values. In certain embodiments, the Irbesartan in the composition is at a concentration sufficient to provide a dose of more than about 300 mg, more than about 375 mg, more than about 450 mg, more than about 525 mg, or more than about 600 mg, including any range in between these values.

Alternatively, in other embodiments, compositions of the invention can include Olmesartan, e.g., where the Olmesartan in the composition is at a concentration sufficient to provide a dose of at least about 5 mg, at least about 10 mg, at least about 15 mg, at least about 20 mg, at least about 25 mg, at least about 30 mg, at least about 35 mg, at least about 40 mg, including any range between these values, or less than about 20 mg, less than about 15 mg, less than about 10 mg including any range between these values. In certain embodiments, the Olmesartan in the composition is at a concentration sufficient to provide a dose of more than about 40 mg, more than about 50 mg, more than about 60 mg, more than about 70 mg, or more than about 40 mg, including any range in between these values.

In certain embodiments, compositions of the invention can include Telmisartan, e.g., where the Telmisartan in the composition is at a concentration sufficient to provide a dose of at least about 5 mg, at least about 10 mg, at least about 15 mg, at least about 20 mg, at least about 25 mg, at least about 30 mg, at least about 35 mg, at least about 40 mg, including any range between these values, or less than about 20 mg, less than about 15 mg, less than about 10 mg, including any range between these values. In certain embodiments, the Telmisartan in the composition is at a concentration sufficient to provide a dose of more than about 80 mg, more than about 100 mg, more than about 120 mg, more than about 140 mg, or more than about 160 mg, including any range in between these values.

In certain embodiments, compositions of the invention can include Valsartan, e.g., where the Valsartan in the composition is present at a concentration sufficient to provide a dose of at least about 5 mg, at least about 10 mg, at least about 15 mg, at least about 20 mg, at least about 25 mg, at least about 30 mg, at least about 35 mg, at least about 40 mg, including any range between these values, or less than about 20 mg, less than about 15 mg, less than about 10 mg, including any range between these values. In certain embodiments, the Valsartan in the composition is at a concentration sufficient to provide a dose of more than about 320 mg, more than about 400 mg, more than about 480 mg, more than about 560 mg, or more than about 640 mg, including any range in between these values.

In some embodiments, the compositions comprise a mixture of 2 or more ARBs. In some aspects, the compositions may comprise about 2 to about 8, or about 2 to about 6, or about 2 to about 4, or 1, 2, 3, 4, 5, 6, 7, 8 or more ARBs as described herein. In some embodiments, methods of the present invention comprise administering 2 or more ARBs. In some aspects the methods comprise administering about 2 to about 8, or about 2 to about 6, or about 2 to about 4, or 1, 2, 3, 4, 5, 6, 7, 8 or more ARBs as described herein. Typically, ARBs are supplied in the form of tablets for oral administration. ARBs each exhibit different pharmacokinetic properties. For example, as shown below in Table 3, the biological half-lives and the bioavailability of ARBs vary widely, with Losartan having the lowest in vivo half-life.

TABLE 3

Comparison of ARB Pharmacokinetics

| Drug | Biological Half-Life | Bioavailability |
| --- | --- | --- |
| Azilsartan | 11 hours | 60% |
| Candesartan | 9 hours | 15% |
| Eprosartan | 5 hours | 13% |

TABLE 3-continued

Comparison of ARB Pharmacokinetics

| Drug | Biological Half-Life | Bioavailability |
|---|---|---|
| Irbesartan | 11-15 hours | 70% |
| Losartan | 2 hours | 33% |
| Olmesartan | 14-16 hours | 29% |
| Telmisartan | 24 hours | 42-58% |
| Valsartan | 6 hours | 25% |

Following administration (e.g., oral or otherwise), the presence and/or the levels of an ARB (or of its metabolites) can be detected in an individual's blood or urine using methods well known to those of skill in the art, including, for example, chromatographic and/or spectroscopic techniques. Details regarding such techniques are described in, e.g., Nakashima et al. (1996) *Blood Press. Suppl.* 2: 62-66; Sica et al. (2005) *Clin. Pharmacokinet.* 44(8): 797-814; Lu et al. (2011) *J. Pharm. Biomed. Anal.* 54(1): 100-105; Yeung et al. (2000) *Int. J. Pharmaceut.* 204: 17-22; Chando et al. (1998) *Drug Metab. Dispos.* 26(5): 408-417; McCarthy et al. (1998) *J. Pharm Biomed. Anal.* 17: 671-677; Ferreirós et al. (2007) *Ther. Drug Monitoring* 29(6): 824-834; González et al. (2002) *J. Chromatography A* 949: 49-60; and others.

Compounds of Formula (I)-(V)

Certain embodiments of the invention relate to compositions and methods where the VEA is a compound of any one of Formulaes (I)-(V). In particular embodiments, a CRC vaccine comprises CRC antigens, a vaccine adjuvant, and a compound of any one of Formulaes (I)-(V).

In certain embodiments, methods described herein comprise administration of compositions comprising a compound of any one of Formulae (I)-(V), and compositions and kits described herein comprise a compound of any one of Formulae (I)-(V). Formulae (I)-(V) are described below.

The present disclosure provides a compound of Formula (I) and compositions comprising a compound of Formula (I):

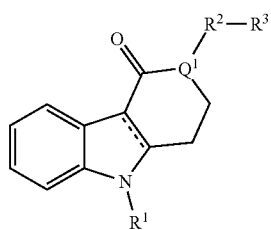

(I)

wherein $R^1$ is hydrogen or $C_{1-6}$ alkyl;

--- is a single bond or double bond;

--- $Q^1$ is N or CH;

$R^2$ is selected from hydrogen and $C_{1-6}$ alkylene, wherein one carbon unit of said alkylene is optionally replaced with —O—, —S—, —SO—, —SO$_2$—, —NR$^a$—, or —C—; wherein $R^a$ is hydrogen or $C_{1-6}$ alkyl; and $R^3$ is hydrogen or an optionally substituted 5-membered heteroaryl ring; wherein the heteroaryl ring is optionally substituted with $C_{1-6}$ alkyl;

or pharmaceutically acceptable salts thereof.

In some embodiments of Formula (I), le is hydrogen. In some embodiments, $R^1$ is $C_{1-6}$ alkyl. In some embodiments, le is methyl or ethyl. In some embodiments, le is methyl.

In some embodiments of Formula (I), --- is a single bond. In some embodiments, --- is a double bond.

In some embodiments of Formula (I), $Q^1$ is N. In some embodiments, $Q^1$ is CH.

In some embodiments of Formula (I), $R^2$ is hydrogen. In some embodiments, $R^2$ is a $C_{1-6}$ alkylene, such as $C_1$ alkylene, $C_2$ alkylene, $C_3$ alkylene, $C_4$ alkylene, $C_5$ alkylene, or $C_6$ alkylene. In some embodiments, $R^2$ is a $C_1$ alkylene. In some embodiments, $R^2$ is $C_{1-6}$ alkylene, wherein one carbon unit of said alkylene is replaced with —O—, —S—, —SO—, —SO$_2$—, —NR$^a$—, or —C—; wherein $R^a$ is hydrogen or $C_{1-6}$ alkyl. In some embodiments, $R^2$ is $C_{1-6}$ alkylene, wherein one carbon unit of said alkylene is replaced with —O—, —S—, —SO—, or —S—$_2$—. In some embodiments, $R^2$ is $C_{1-6}$ alkylene, wherein one carbon unit of said alkylene is replaced with —NR$^a$—; wherein $R^a$ is hydrogen or $C_{1-6}$ alkyl. In some embodiments, $R^2$ is $C_{1-6}$ alkylene, wherein one carbon unit of said alkylene is replaced with —C—.

In some embodiments of Formula (I), $R^3$ is hydrogen. In some embodiments, $R^3$ is an optionally substituted 5-membered heteroaryl ring; wherein the heteroaryl ring is optionally substituted with $C_{1-6}$ alkyl. In some embodiments, $R^3$ is an optionally substituted 5-membered heteroaryl ring containing one, two, three, or four heteroatoms. In certain instances, the $R^3$ heteroaryl ring contains one heteroatom. In certain instances, the $R^3$ heteroaryl ring contains two heteroatoms. In certain instances, the $R^3$ heteroaryl ring contains three heteroatoms. In certain instances, the $R^3$ heteroaryl ring contains four heteroatoms. In certain instances, the $R^3$ heteroaryl ring contains at least one heteroatom selected from nitrogen, sulfur, and oxygen. In certain instances, the $R^3$ heteroaryl ring contains two heteroatoms selected from nitrogen, sulfur, and oxygen. In certain instances, the $R^3$ heteroaryl ring contains two nitrogen heteroatoms. In certain instances, the $R^3$ heteroaryl ring contains carbon, nitrogen, and sulfur ring members. In certain instances, the $R^3$ heteroaryl ring contains carbon and nitrogen ring members. In certain instances, the $R^3$ heteroaryl ring contains carbon, nitrogen, and oxygen ring members.

In certain instances, the $R^3$ heteroaryl ring is furanyl, thiophenyl, pyrrolyl, oxazolyl, thiazolyl, imidazolyl, thiadiazolyl, oxadiazolyl, triazolyl, or tetrazolyl, each optionally substituted with $C_{1-6}$alkyl, as described for the $R^3$ heteroaryl ring. In certain instances, the $R^3$ heteroaryl ring is selected from the following:

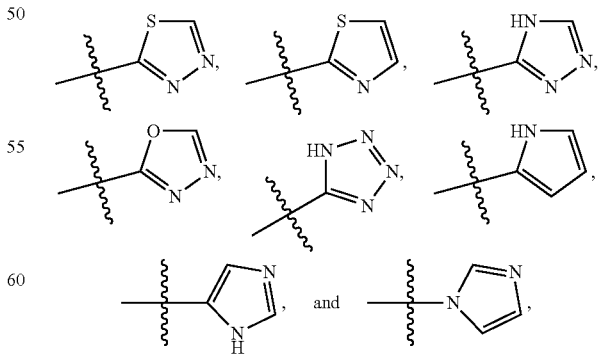

each optionally substituted with $C_{1-6}$ alkyl, as described for the $R^3$ heteroaryl ring. In certain instances, the $R^3$ heteroaryl ring is

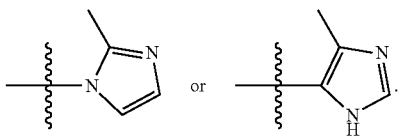 or 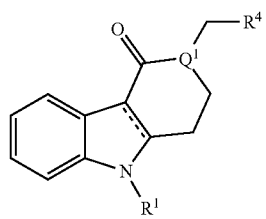

The present disclosure provides a compound of Formula (II) and compositions comprising a compound of Formula (II):

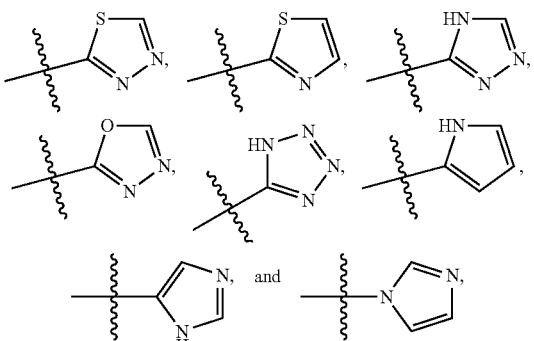

wherein
$R^1$ is hydrogen or $C_{1-6}$ alkyl;
=== is a single bond or double bond;
$Q^1$ is N or CH; and
$R^4$ is an optionally substituted 5-membered heteroaryl ring; wherein the heteroaryl ring is optionally substituted with $C_{1-6}$ alkyl;

or pharmaceutically acceptable salts thereof.

In some embodiments of Formula (II), le is hydrogen. In some embodiments, $R^1$ is $C_{1-6}$ alkyl. In some embodiments, le is methyl or ethyl. In some embodiments, le is methyl.

In some embodiments of Formula (II), === is a single bond. In some embodiments, === is a double bond.

In some embodiments of Formula (II), $Q^1$ is N. In some embodiments, $Q^1$ is CH.

In some embodiments of Formula (II), $R^4$ is an optionally substituted 5-membered heteroaryl ring; wherein the heteroaryl ring is optionally substituted with $C_{1-6}$alkyl. In some embodiments, $R^4$ is an optionally substituted 5-membered heteroaryl ring containing one, two, three, or four heteroatoms. In certain instances, the $R^4$ heteroaryl ring contains one heteroatom. In certain instances, the $R^4$ heteroaryl ring contains two heteroatoms. In certain instances, the $R^4$ heteroaryl ring contains three heteroatoms. In certain instances, the $R^4$ heteroaryl ring contains four heteroatoms. In certain instances, the $R^4$ heteroaryl ring contains at least one heteroatom selected from nitrogen, sulfur, and oxygen. In certain instances, the $R^4$ heteroaryl ring contains two heteroatoms selected from nitrogen, sulfur, and oxygen. In certain instances, the $R^4$ heteroaryl ring contains two nitrogen heteroatoms. In certain instances, the $R^4$ heteroaryl ring contains carbon, nitrogen, and sulfur ring members. In certain instances, the $R^4$ heteroaryl ring contains carbon and nitrogen ring members. In certain instances, the $R^4$ heteroaryl ring contains carbon, nitrogen, and oxygen ring members.

In certain instances, the $R^4$ heteroaryl ring is furanyl, thiophenyl, pyrrolyl, oxazolyl, thiazolyl, imidazolyl, thiadiazolyl, oxadiazolyl, triazolyl, or tetrazolyl, each optionally substituted with $C_{1-6}$ alkyl, as described for the $R^4$ heteroaryl ring. In certain instances, the $R^4$ heteroaryl ring is selected from the following:

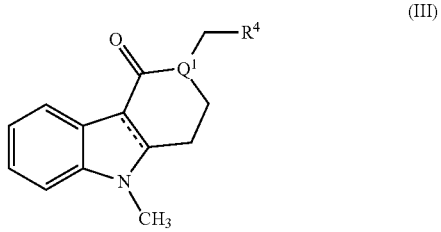

each optionally substituted with $C_{1-6}$alkyl, as described for the $R^3$ heteroaryl ring. In certain instances, the $R^4$ heteroaryl ring is

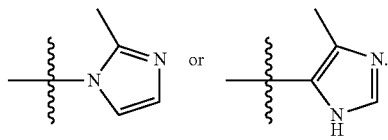

The present disclosure provides a compound of Formula (III) and compositions comprising a compound of Formula (III):

(III)

wherein
=== is a single bond or double bond;
$Q^1$ is N or CH; and
$R^4$ is an optionally substituted 5-membered heteroaryl ring; wherein the heteroaryl ring is optionally substituted with $C_{1-6}$ alkyl;

or pharmaceutically acceptable salts thereof.

In some embodiments of Formula (III), === is a single bond. In some embodiments, === is a double bond.

In some embodiments of Formula (III), $Q^1$ is N. In some embodiments, $Q^1$ is CH.

In some embodiments of Formula (III), $R^4$ is an optionally substituted 5-membered heteroaryl ring; wherein the heteroaryl ring is optionally substituted with $C_{1-6}$alkyl. In some embodiments, $R^4$ is an optionally substituted 5-membered heteroaryl ring containing one, two, three, or four heteroatoms. In certain instances, the $R^4$ heteroaryl ring contains one heteroatom. In certain instances, the $R^4$ heteroaryl ring contains two heteroatoms. In certain instances, the $R^4$ heteroaryl ring contains three heteroatoms. In certain instances, the $R^4$ heteroaryl ring contains four heteroatoms. In certain instances, the $R^4$ heteroaryl ring contains at least one heteroatom selected from nitrogen, sulfur, and oxygen. In certain instances, the $R^4$ heteroaryl ring contains two heteroatoms selected from nitrogen, sulfur, and oxygen. In certain instances, the $R^4$ heteroaryl ring contains two nitrogen heteroatoms. In certain instances, the $R^4$ heteroaryl ring contains carbon, nitrogen, and sulfur ring members. In certain instances, the $R^4$ heteroaryl ring contains carbon and nitrogen ring members. In certain instances, the $R^4$ heteroaryl ring contains carbon, nitrogen, and oxygen ring members.

In certain instances, the $R^4$ heteroaryl ring is furanyl, thiophenyl, pyrrolyl, oxazolyl, thiazolyl, imidazolyl, thiadiazolyl, oxadiazolyl, triazolyl, or tetrazolyl, each optionally substituted with $C_{1-6}$alkyl, as described for the $R^4$ heteroaryl ring. In certain instances, the $R^4$ heteroaryl ring is selected from the following:

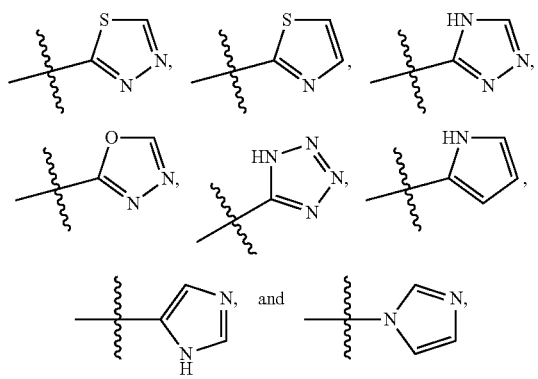

each optionally substituted with $C_{1-6}$alkyl, as described for the $R^3$ heteroaryl ring. In certain instances, the $R^4$ heteroaryl ring is

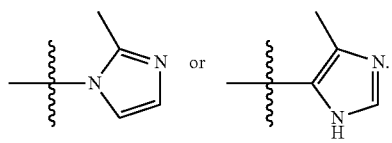

The present disclosure provides a compound of Formula (IV) and compositions comprising a compound of Formula (IV):

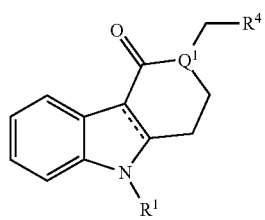

(IV)

wherein
$R^1$ is hydrogen or $C_{1-6}$ alkyl;
═ is a single bond or double bond;
$Q^1$ is N or CH; and $R^4$ is selected from

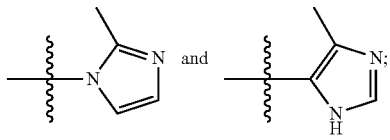

or pharmaceutically acceptable salts thereof.

In some embodiments of Formula (IV), 1e is hydrogen. In some embodiments, $R^1$ is $C_{1-6}$ alkyl. In some embodiments, 1e is methyl or ethyl. In some embodiments, 1e is methyl.

In some embodiments of Formula (IV), ═ is a single bond. In some embodiments, ═ is a double bond.

In some embodiments of Formula (IV), $Q^1$ is N. In some embodiments, $Q^1$ is CH.

In some embodiments of Formula (IV), $R^4$ is

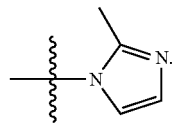

In some embodiments, $R^4$ is

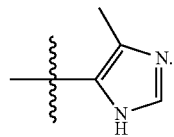

The present disclosure provides a compound of Formula (V) and compositions comprising a compound of Formula (V):

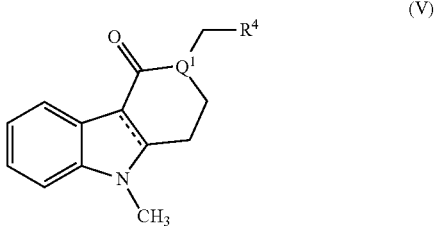

(V)

wherein
═ is a single bond or double bond;
$Q^1$ is N or CH; and
$R^4$ is selected from

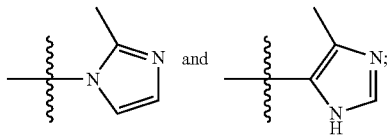

or pharmaceutically acceptable salts thereof.

In some embodiments of Formula (V), ═ is a single bond. In some embodiments, ═ is a double bond.

In some embodiments of Formula (V), $Q^1$ is N. In some embodiments, $Q^1$ is CH.

In some embodiments of Formula (V), $R^4$ is

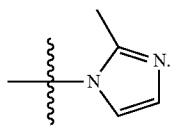 [SMILES: *n1ccnc1C]

In some embodiments, $R^4$ is

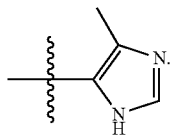

It is appreciated that certain features of the invention, which are, for clarity, described in the context of separate embodiments, may also be provided in combination in a single embodiment. Conversely, various features of the invention, which, for brevity, are described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

Particular compounds of interest are shown below:

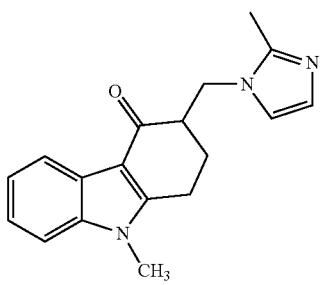

Ondansetron;
9-methyl-3-((2-methyl-1H-imidazol-1-yl)methyl)-2,3-dihydro-1H-carbazol-4(9H)-one

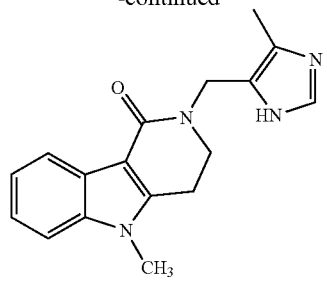

Alosetron;
5-methyl-2-((4-methyl-1H-imidazol-5-yl)methyl)-2,3,4,4a,5,9b-hexahydro-1H-pyrido[4,3-b]indol-1-one Alosetron can be used in the management of severe diarrhea-predominant irritable bowel syndrome (IBS). Ondansetron can be prescribed to treat and/or prevent chemotherapy-induced nausea and vomiting (CINV). Ondansetron has been indicated in the prevention and treatment of radiation-induced nausea and vomiting (RINV), and post-operative nausea and vomiting (PONV). The benefits of Ondansetron treatment have also been tested for a variety of other diseases and disorders, including, e.g., motion sickness (Levine et al. (2000) Aviat Space Environ Med. 71: 1111-1114; Muth et al. (2007) Aviat Space Environ Med. 78: 686-92); lesional vestibular disorder (European Patent Application No. 2432467 A1 and US Patent Application Publication 2012/0064094); anti-psychotic induced tardive dyskinesia in people with schizophrenia (Zullino et al. (2001) Am. J. Psychiatry 158: 657-8 and Sirota et al. (2000) Am. J. Psychiatry 157: 287-289); and schizophrenia (Zhang et al. (2006) Schiz Res 88: 102-110). Other medical conditions that may be treated using ondansetron include, e.g., gastroenteritis, pediatric gastroenteritis, opioid-induced nausea, nausea and vomiting of pregnancy, and obsessive-compulsive disorder (Broocks et al. (1998) Psychiatry Res. 79: 11-20).

Ondansetron and Alosetron are each known by a number of trade names, the most common of which are listed in Table 4 below.

TABLE 4

| Trade Names | |
|---|---|
| Trade Names | |
| Alosetron | Lotronex ® |
| Ondansetron | Doran ®, Lupisetron ®, Mylan Ondansetron, Myset ®, Ranidom ®, Vomicare ®, Vomiven ®, Zofran ®, Zofran ODT ®, Zuplenz ® |

Accordingly, in certain embodiments, the compositions of the invention include Ondansetron. In certain embodiments, the composition is administered orally. In certain embodiments, Ondansetron in the orally administered composition is at a concentration sufficient to provide a dose of at least about 0.5 mg, at least about 1 mg, at least about 2 mg, at least about 3 mg, at least about 4 mg, at least about 5 mg, at least about 6 mg, at least about 7 mg, at least about 8 mg, at least about 10 mg, or less than about 12 mg, or less than about 18 mg, or less than about 24 mg of Ondansetron, including any range in between these values. In certain embodiments, the Ondansetron in the orally administered composition is at a concentration sufficient to provide a dose of more than about 24 mg, more than about 26 mg, more than about 28 mg, more than about 30 mg, more than about 32 mg, or more than about 34 mg Ondansetron, including any range in between these values.

In certain embodiments, compositions of the invention are administered intravenously. In certain embodiments, compositions for intravenous administration can include Ondansetron, e.g., at a concentration sufficient to provide a dose of at least about 0.5 mg/kg/day, at least about 0.75 mg/kg/day, at least about 1.0 mg/kg/day, at least about 1.5 mg/kg/day, at least about 2.0 mg/kg/day, at least about 2.5 mg/kg/day, at least about 3.0 mg/kg/day, at least about 3.5 mg/kg/day, at least about 4.0 mg/kg/day, at least about 4.5 mg/kg/day, at least about 5.0 mg/kg/day, at least about 5.5 mg/kg/day, at least about 6.0 mg/kg/day, at least about 6.5 mg/kg/day, at least about 7.0 mg/kg/day, at least about 7.5 mg/kg/day, at least about 8.0 mg/kg/day, or less than about 8.5 mg/kg/day of Ondansetron, including any range between these values.

In certain embodiments, the invention provides compositions that can include Alosetron, e.g., where the Alosetron in the composition is at a concentration sufficient to provide a dose of at least about 0.1 mg, at least about 0.2 mg, at least about 0.3 mg, at least about 0.4 mg, at least about 0.6 mg, at least about 0.8 mg, at least about 0.9 mg, at least about 1 mg, including any range between these values, or less than about 0.5 mg or less than about 0.7 mg or less than about 0.9 mg, or less than about 1 mg of Alosetron, including any range between these values. In certain embodiments, the Alosetron in the composition is at a concentration sufficient to provide a dose of more than about 2 mg, more than about 3 mg, more than about 4 mg, more than about 5 mg, or more than about 6 mg Alosetron, including any range in between these values.

Ondansetron and Alosetron are supplied in the form of tablets or solutions for oral administration. In one embodiment, Ondansetron is also supplied in solution form for parenteral administration. Ondansetron and Alosetron each exhibit different pharmacokinetic properties. For example, the biological half-life of Alosetron is about 1.5 to about 1.7 hours, and the biological half-life of Ondansetron is about 3.9 hours.

Following administration (e.g., oral, intramuscular, subcutaneous, or otherwise), the presence and/or the levels of a compound of Formula (I) (or of its metabolites) can be detected in an individual's blood or urine using methods well known to those of skill in the art, including, for example, chromatographic and/or spectroscopic techniques. Details regarding such techniques are described in, e.g., Somers et al. (2007) Xenobiotica 37: 855-869; Koch et al. (2002) Br J Clin Pharmacol. 53: 238-242; Xu et al. (2000) J Mass Spectrom 35: 1329-1334; Roila et al. (1995) Clin Pharmacokinet 29: 95-103; and others.

CSC Vaccine Compositions

The present invention includes pharmaceutical compositions comprising a CSC vaccine, which may further comprise one or more pharmaceutically acceptable carrier, diluent or excipient. Compositions may thus be pharmaceutically acceptable. Such diluents, excipients and carriers are known and available in the art. Compositions may be in an aqueous form. Alternatively, e.g., prior to administration, the composition may have been in a non-aqueous form. For instance, although some vaccines are manufactured in aqueous form, then filled and distributed and administered also in aqueous form, other vaccines are lyophilized during manufacture and are reconstituted into an aqueous form at the time of use. Thus a composition of the invention may be dried, such as a lyophilized formulation.

In certain embodiments, pharmaceutical compositions of CSC vaccines are formulated for parenteral or oral delivery, e.g., formulated for intravenous, subcutaneous, intramuscular, or oral delivery. In particular embodiments, the compositions may be delivered orally, by injection, intramuscularly (IM) or subcutaneously (SC).

The composition may include preservatives such as thiomersal or 2-phenoxyethanol, or it may be substantially free from (i.e. less than 5 ug/ml) mercurial material e.g., thiomersal-free. A composition may include a temperature protective agent. To control tonicity, it may include a physiological salt, such as a sodium salt. Sodium chloride (NaCl) may be present at between 1 and 20 mg/ml e.g. about 10+/−2 mg/ml NaCl. Other salts that may be present include potassium chloride, potassium dihydrogen phosphate, disodium phosphate dehydrate, magnesium chloride, calcium chloride, etc. Compositions may have an osmolality of between 200 mOsm/kg and 400 mOsm/kg, e.g., between 240-360 mOsm/kg, or within the range of 290-310 mOsm/kg. Compositions may include one or more buffers. Typical buffers include: a phosphate buffer; a Tris buffer; a borate buffer; a succinate buffer; a histidine buffer (particularly with an aluminium hydroxide adjuvant); or a citrate buffer. Buffers will typically be included in the 5-20 mM range. The pH of a composition will generally be between 5.0 and 8.1, and more typically between 6.0 and 8.0 e.g. 6.5 and 7.5, or between 7.0 and 7.8. The composition is preferably sterile. The composition is preferably non-pyrogenic e.g. containing <1 EU (endotoxin unit, a standard measure) per dose, and preferably <0.1 EU per dose. The composition is preferably gluten free.

The composition may be present in one or more containers or vials, e.g., single use or multiuse containers or vials. The composition may be present in a kit comprising a container comprising a CSC vaccine composition. In various embodiments, the kit or composition may include material for a single immunization, or may include material for multiple immunizations (i.e., a "multidose" kit). The inclusion of a preservative may be preferred in multidose arrangements. As an alternative (or in addition) to including a preservative in multidose compositions, the compositions may be contained in a container having an aseptic adaptor for removal of material. In particular embodiments, a vaccine of the present invention is administered at a dosage of about 0.1 ml to about 5 ml, about 0.2 ml to about 2 ml, about 0.5 ml to about 2 ml, or about 1 ml to 2 ml. In certain embodiments, human vaccines are administered in a dosage volume of about 0.5 ml, although a half dose (i.e. about 0.25 ml) may be administered to children.

Methods of Treatment

The present invention includes methods of treating or preventing a tumor or cancer in a subject in need thereof, comprising providing to the subject an effective amount of a CSC vaccine. It also includes related methods of inducing an immune response against a tumor or cancer in a subject in need thereof, comprising providing to the subject an effective amount of a CSC vaccine. It also includes related methods of inhibiting tumor growth, reducing tumor size, and inhibiting tumor metastasis in a subject in need thereof comprising providing to the subject an effective amount of a CSC vaccine. In particular embodiments, tumor growth, tumor size, or tumor metastasis is inhibited or reduced by at least 10%, 20%, 50%, 75%, or 90% as compared to in the absence of treatment with a CSC vaccine of the present. In particular embodiments, the subject has been diagnosed with a tumor or tumor metastasis, whereas in other embodiments, the subject is considered to be a risk of developing a tumor or tumor metastasis.

The tumor may be any type of tumor or cancer, including but not limited to solid tumors and liquid tumors. In particular embodiments, the tumor is a breast cancer, lung cancer, prostate cancer, colorectal cancer (e.g., colon carcinoma), brain cancer, esophageal cancer, stomach cancer, bladder cancer, pancreatic cancer, cervical cancer, head and neck cancer, ovarian cancer, melanoma, leukemia, myeloma, lymphoma, glioma, Non-Hodgkin's'lymphoma, leukemia, multiple myeloma or multidrug resistant cancer.

In certain embodiments, the CSC vaccine is provided orally or parenterally, e.g., intravenously, subcutaneously, or intramuscularly.

In particular amounts, an effective amount of the CSC vaccine comprises, e.g.: about 100 ug to about 500 ug (or 100 ug to about 200 ug) of CSC antigen; about 1 ml to about 5 ml (e.g., about 1 ml) of adjuvant; optionally, about 100 ug to about 20 mg, about 100 ug to about 10 mg, about 100 ug to about 1 mg, or about 100 ug to about 250 ug (e.g., about 250 ug) of an agent that enhances cellular immunity; and, optionally about 1% to about 20%, about 2% to about 15%, about 2.5% to about 10%, about 5% to about 10%, or about 5% (v/v) of a cellular adhesion agent, such as carboxymethyl cellulose of a PEG. In particular embodiments, the effective amount of the CSC vaccine comprises: 100 to 500 ug of CSC antigen; 1-4 ml of cationic liposome-DNA complexes; and about 100 ug to about 20 mg, about 100 ug to about 10 mg, about 100 ug to about 1 mg, or about 100 ug to about 250 ug of a CCR2 antagonist. In particular embodiments, the CCR2 antagonist is RS102895 or RS504393. In particular embodiments, it further comprises about 5% to about 10% (v/v) of carboxymethyl cellulose. In certain embodiments, these effective amounts are present in a 1 ml vaccine.

In certain embodiments, a CSC vaccine comprises about 100 ug of CSC antigen, about 100 ug of CLDC adjuvant, and about 250 ug of RS102895. In certain embodiments, a CSC vaccine comprises about 100 ug of CSC antigen, about 100 ug of CLDC adjuvant, and about 100 ng to about 20 mg of RS102895. In particular embodiments, it further comprises about 5% to about 10% (v/v) of carboxymethyl cellulose.

In certain embodiments, the composition is administered orally. In certain embodiments, RS102895 or RS504393 in the orally administered composition is at a concentration sufficient to provide a dose of at least about 0.1 mg, at least about 0.2 mg, at least about 0.25 mg, at least about 0.5 mg, at least about 1 mg, at least about 5 mg, at least about 10 mg, or at least about 20 mg of RS102895 or RS504393, including any range in between these values.

For example, the invention provides CSC vaccines that can include CSC antigens, and RS102895 or RS504393, where the RS102895 or RS504393 in the composition is at a concentration sufficient to provide a dose of at least about 0.1 mg, at least about 0.2 mg, at least about 0.3 mg, at least about 0.4 mg, or less than about 0.5 mg RS102895 or RS504393, including any range between these values. In certain embodiments, the RS102895 or RS504393 in the composition is at a concentration sufficient to provide a dose of more than about 2 mg, more than about 3 mg, more than about 4 mg, more than about 5 mg, or more than about 6 mg RS102895 or RS504393, including any range in between these values. In certain embodiments, the RS102895 or RS504393 in the composition is at a concentration sufficient to provide a dose of at least about 1 mg, at least about 5 mg, at least about 10 mg, or at least about 20 mg.

CSC vaccine may be provided according to various dosing regimens. In certain embodiments, CSC vaccine is provided once or more than once, e.g., two, three, four, five, six, seven, eight, nine, ten or more times. In particular embodiments, CSC antigen may be provided daily, every other day, twice a week, weekly, every other week, once a month, or once every other month.

EXAMPLES

Example 1

Enrichment for Cancer Stem Cell In Vitro

The ability of the cell culture conditions of the present invention to induce CSCs was demonstrated in several cell lines.

CT26 colon carcinoma cells were grown under stem cell enrichment conditions ("CSC cult") for generation of tumor cells that upregulate expression of stem cell markers, compared to tumor cells cultured under conventional tissue culture conditions ("parent"). CSC culture conditions included growth in serum-free medium supplemented with 1× B-27 mix (Gibco® B27® Supplements available from Gibco, ThermoFisher Scientific), 5 ng/ml bFGF and 5 ng/ml EGF and 1× Glutamax, under non-adherent conditions. Parent conditions included growth in medium (MEME with 1% non-essential amino acids and penicillin and streptomycin) containing 10% fetal bovine serum, under adherent conditions.

Figure 2:
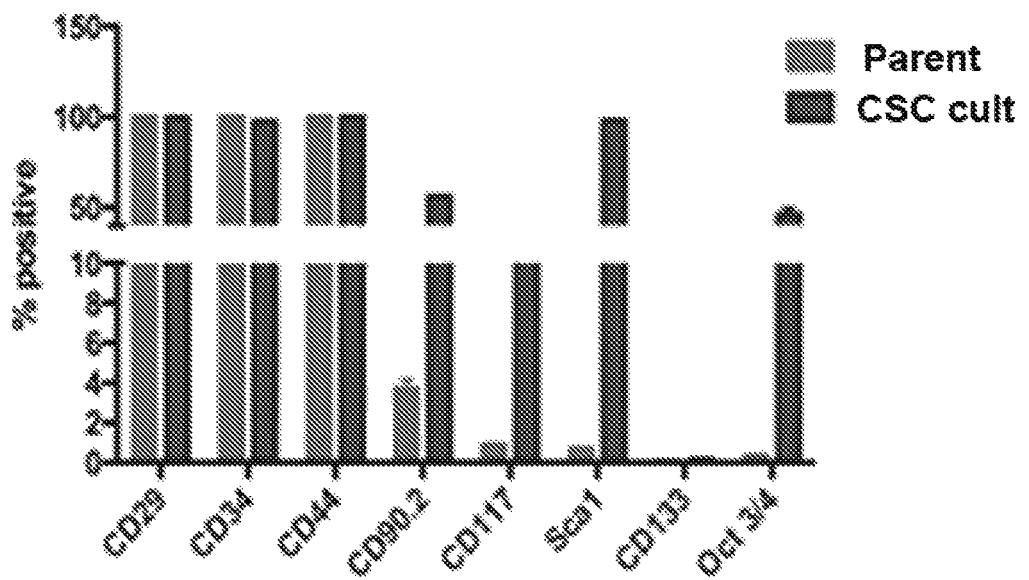
FIG. 2 is a graph showing enrichment for cancer stem cells in vitro. CT26 colon carcinoma cells were grown under tumor stem cell enrichment conditions (serum-free DME medium, B27 supplement, 10 ng/ml FGF, and 10 ng/ml EGF) ("CSC cult"; right) for generation of tumor cells that upregulate expression of stem cell markers, compared to tumor cells cultured under conventional tissue culture conditions ("parent"; left). The expression of cancer stem cell markers by tumor cells grown under the two different cell culture conditions was determined by flow cytometry. The tumor cell lysates used as antigens for the tumor CSC and mature tumor cell vaccines were prepared from tumor cells grown under the two different culture conditions. For each stem cell marker shown, the left bar is "parent" and the right bar is "CSC cult."

The expression of CSC markers by tumor cells grown under these two different cell culture conditions was determined by flow cytometry analysis using antibodies specific for the cell surface markers, CD29, CD34, CD44, CD90.2, CD117, Sca1, CD133 and Oct3/4. As shown in FIG. 2, the cells grown under CSC cult conditions showed substantially increased expression of stem cell markers as compared to the cells grown under parent conditions.

CSC vaccine was prepared from these CSC cult tumor cells and parent tumor cells by freeze-thaw lysing the cultured tumor cells to produce tumor lysates, which were used as antigens in CSC vaccines used in animal studies.

Figure 4A:
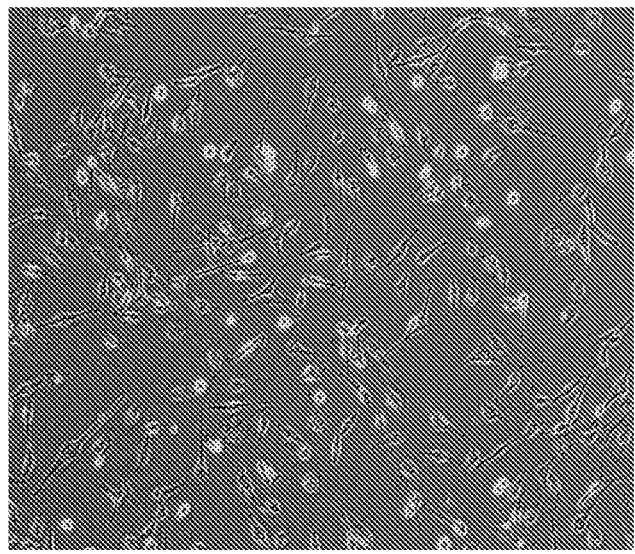
FIGS. 4A and 4B are photomicrographs demonstrating the appearance of cells under standard tissue culture conditions (FIG. 4A) or stem cell culture conditions (FIG. 4B). When CT26 murine colon carcinoma tumor cells were grown under normal tissue culture conditions (FIG. 4A) and then switched to cancer stem cell (CSC) conditions (FIG. 4B), their phenotype changed drastically. They were no longer adherent, they formed tight spheres, and their cell surface phenotype changed (see FIG. 5). The cell culture conditions ("tumor spheroid culture") used to generate CSC for vaccine preparation consisted of the following: serum-free basal medium supplemented with insulin-selenium-transferrin mix, and 5 ng/ml basic FGF and 5 ng/ml EGF, along with culture on non-stick tissue culture plates.
Figure 4B:
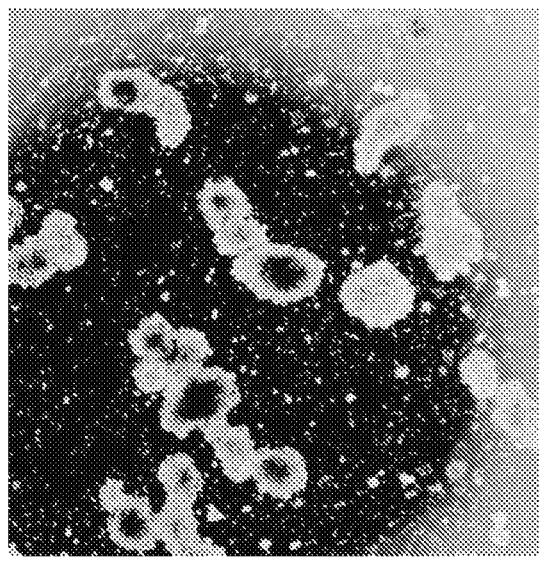
Figure 5:
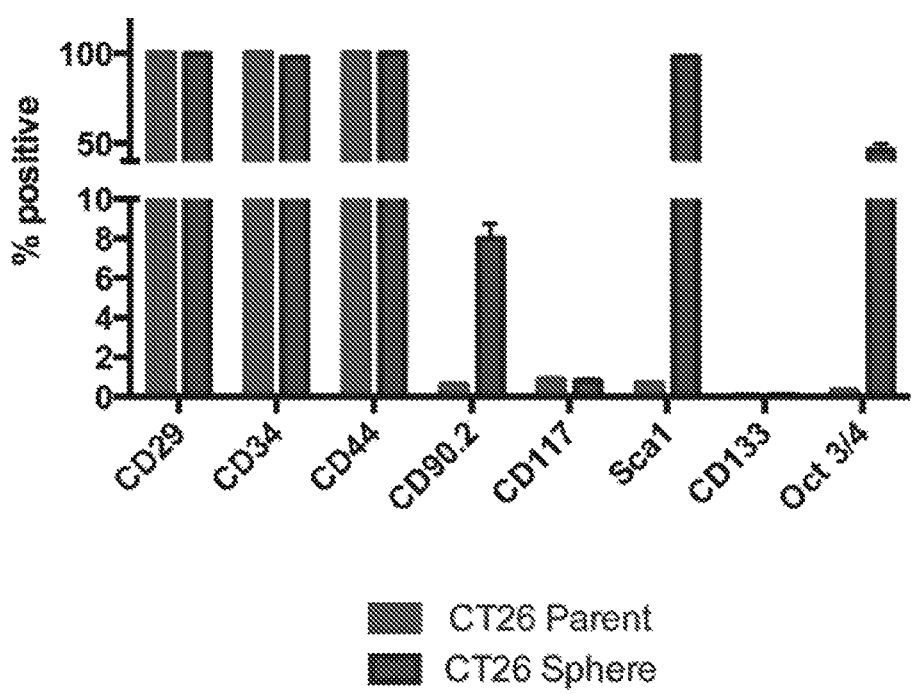
FIG. 5 is a graph showing that culture in tumor spheroid conditions (i.e., stem cell conditions) enriches for CSC expressing stem cell markers. Murine colon carcinoma CT26 tumor cells were cultured under standard conditions ("CT26 parent"; left) or CSC conditions ("CT26 sphere"; right) to generate CSC enriched cultures. The surface phenotype of the "parent" and "sphere" cultures was assessed by flow cytometry. Enrichment for CSC by culture in tumor sphere conditions resulted in significant upregulation of the stem cell markers including CD90, Sca1, CS133, and Oct 3/4. For each stem cell marker shown, the left bar indicates "CT26 parent" and the right bar indicates "CT26 sphere."

Other CSC cell culture conditions ("tumor spheroid culture") used to generate CSC for vaccine preparation are described above. When CT26 murine colon carcinoma tumor cells grown under normal tissue culture conditions (e.g., growth in MEME with 1% non-essential amino acids and penicillin and streptomycin containing 10% fetal bovine serum, under adherent conditions) (FIG. 4A) were switched to tumor spheroid culture conditions (FIG. 4B), their phenotype changes drastically. Cells cultured under these conditions were no longer adherent, they formed tight spheres, and their cell surface phenotype changed, including significant upregulation of the stem cell markers CD90, Sca1, CS133 and Oct3/4 (FIG. 5).

Example 2

Effect of Immunization with CSC Vaccine in Animal Models of Cancer

The protective effect of treatment with a CSC vaccine of the invention was determined in several animal models of cancer.

Mice (n=5 per group) with established subcutaneous CT26 tumors were immunized with the CSC vaccine or with a conventional tumor vaccine, prepared using lysates from tumor cells grown under conventional adherent conditions with tissue culture medium containing fetal bovine serum. or were unvaccinated. The CSC vaccine consisted of 50 ug CSC antigen mixed with 200 ul CLDC adjuvant plus 250 mg/ml of RS102895 (or other vaccine enhancing agent). The conventional tumor vaccine consisted of 50 ug non-CSC tumor antigen mixed with 200 ul CLDC adjuvant plus 250 mg/ml of RS102895 (or other vaccine enhancing agent). Vaccinations were administered SC and repeated weekly. Tumor dimensions were determined at 3-day intervals. As shown in FIG. 1, immunization with the CSC vaccine (CSC vax; triangle) triggered significant inhibition of tumor growth, compared to animals immunized with a conventional tumor vaccine (Tumor vax; square) or not vaccinated (No vax, circle). The vaccines were prepared by freeze-thaw lysing tumor cells to prepare tumor lysates, then combining the lysate with cationic liposome-non-coding plasmid DNA adjuvant.

Figure 3:
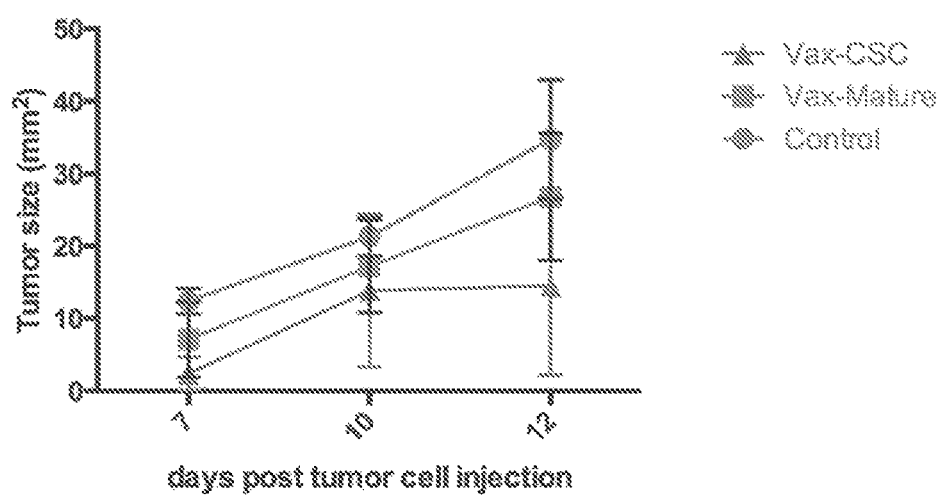
FIG. 3 is a graph showing the effects of CSC vaccination on tumor growth in a mouse breast cancer model. Mice with established orthotopic breast cancers (PyMT cell line) were vaccinated once weekly with vaccines prepared using either CSC antigens (prepared as noted above for stem cell enrichment conditions) (Vax-CSC; triangles) or antigens prepared from mature tumor cells (Vax-Mature; squares). Control animals were not vaccinated (Control; circles). Tumor growth was monitored every 3 days by direct tumor measurements. Tumor growth was significantly inhibited in mice vaccinated with the CSC vaccine compared to animals vaccinated with the mature tumor cell vaccine.

The effect of CSC vaccination on tumor growth in a mouse breast cancer model was also examined. Mice with established orthotopic breast cancers (PyMT cell line) were vaccinated once weekly with vaccines prepared using either CSC antigens prepared and used as described above for the CT26 model (Vax-CSC; triangles) or antigens prepared from mature tumor cells (Vax-Mature; squares). Control animals were not vaccinated (Control; circles). Tumor growth was monitored every 3 days by direct tumor measurements. Tumor growth was significantly inhibited at day 12 in mice vaccinated with the CSC vaccine compared to animals vaccinated with the mature tumor cell vaccine (FIG. 3).

Figure 6A:
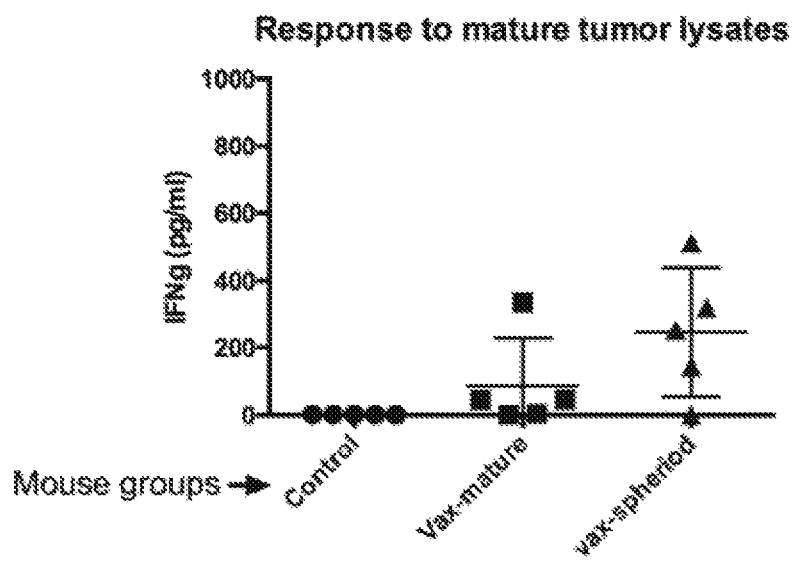
FIGS. 6A and 6B are graphs showing that tumor immune responses are increased when animals are vaccinated with CSC vaccines versus conventional tumor vaccines. Mice (n=4-5 per group) were vaccinated weekly for 3 immunizations with either standard tumor lysate vaccines ("Vax-mature"; squares) or CSC lysate vaccines ("vax-spheroid"; triangles). Spleen cells from unvaccinated mice and mice immunized with non-stem cell or CSC vaccines were then re-stimulated in vitro with tumor cell culture lysates to assess the magnitude of T cell immune responses. Unvaccinated mice did not generate measurable immune responses. Mice vaccinated with the CSC vaccine ("vax-spheroid") mounted much stronger immune responses (IFN-gamma release) than did mice vaccinated with conventional tumor vaccines. This was true whether the spleen cells were restimulated with tumor lysates from non-stem cell tumors (FIG. 6A), or with lysates from in vitro grown CSC ("spheroid tumor lysates"
Figure 6B:
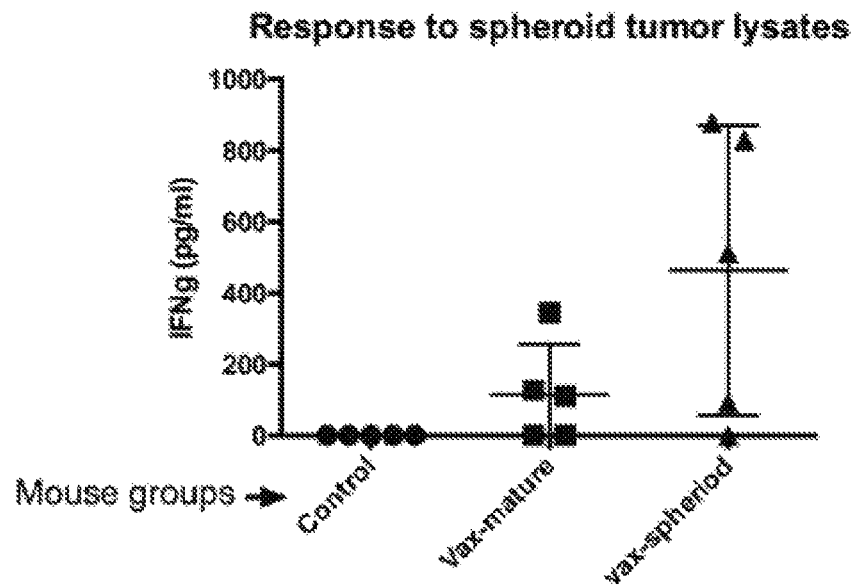

Tumor immune responses in mice vaccinated with CSC vaccine or conventional tumor vaccines was compared. Mice (n=4-5 per group) were vaccinated weekly for 3 immunizations with either standard tumor lysate vaccines ("Vax-mature"; squares) or CSC lysate vaccines ("vax-spheroid"; triangles). Spleen cells from unvaccinated mice and mice immunized with non-stem cell or CSC vaccines were then restimulated in vitro with cell culture lysates to assess the magnitude of T cell immune responses, as measured by release of interferon-gamma (IFN-gamma). Unvaccinated mice did not generate immune responses. Mice vaccinated with the CSC vaccine ("vax-spheroid") mounted much stronger immune responses (IFN-gamma release) than did mice vaccinated with conventional tumor vaccines. This was true whether the spleen cells were restimulated with tumor lysates from non-stem cell tumors (FIG. 6A), or with lysates from in vitro grown CSC ("spheroid tumor lysates"; FIG. 6B). These data show that tumor immune responses are increased when animals are vaccinated with CSC vaccines versus conventional tumor vaccines.

Figure 7:
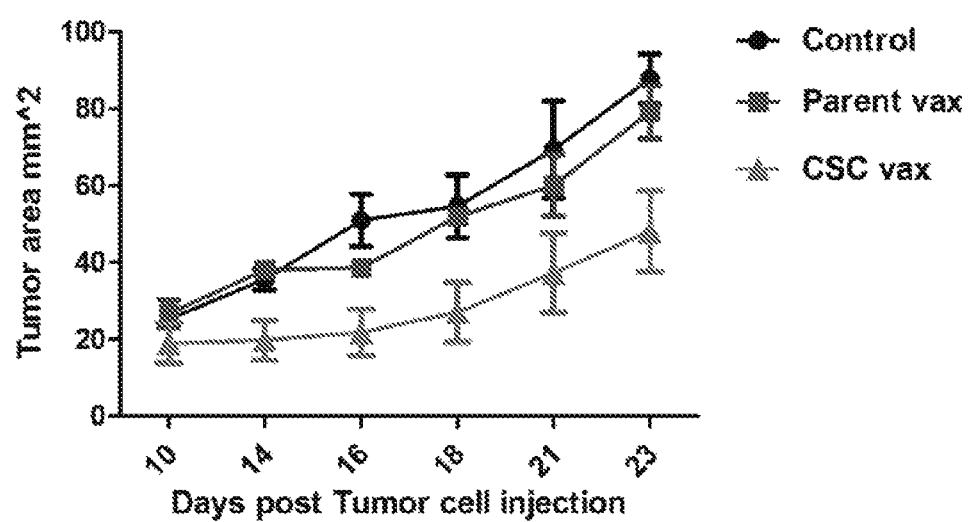
FIG. 7 is a graph showing that immunization against CSC antigens stimulates protective immunity against PyMT breast cancer tumors. Tumors were induced in mice (n=5 per group) by SC injection of PyMT tumor cells. One group of mice was unvaccinated (control; circles), whereas one group was vaccinated weekly with tumor lysates prepared from conventionally grown PyMT tumor cells (parent vax; squares). The third group of animals was immunized with lysates prepared from PyMT tumor cells grown under stem cell conditions (CSC vax; triangles). Tumor growth was significantly inhibited by immunization with the CSC vax.

The ability of immunization against CSC antigens to stimulate protective immunity against PyMT breast cancer tumors was also shown. Tumors were induced in mice (n=5 per group) by SC injection of PyMT tumor cells. One group of mice was unvaccinated (control; circles), whereas one group was vaccinated weekly with tumor lysates prepared from conventionally grown PyMT tumor cells (parent vax; squares). The third group of animals was immunized with lysates prepared from PyMT tumor cells grown under stem cell conditions CSC culture conditions included growth in serum-free medium supplemented with 1× B-27 mix, 5 ng/ml bFGF and 5 ng/ml EGF and 1× Glutamax, under non-adherent conditions. Parent conditions included growth in medium (MEME with 1% non-essential amino acids and penicillin and streptomycin) containing 10% fetal bovine serum, under adherent conditions. (CSC vax; triangles). Tumor growth was significantly inhibited by immunization with the CSC vax (FIG. 7). All data points for days 14-23 were determined by repeated measurement by ANOVA.

Figure 8:
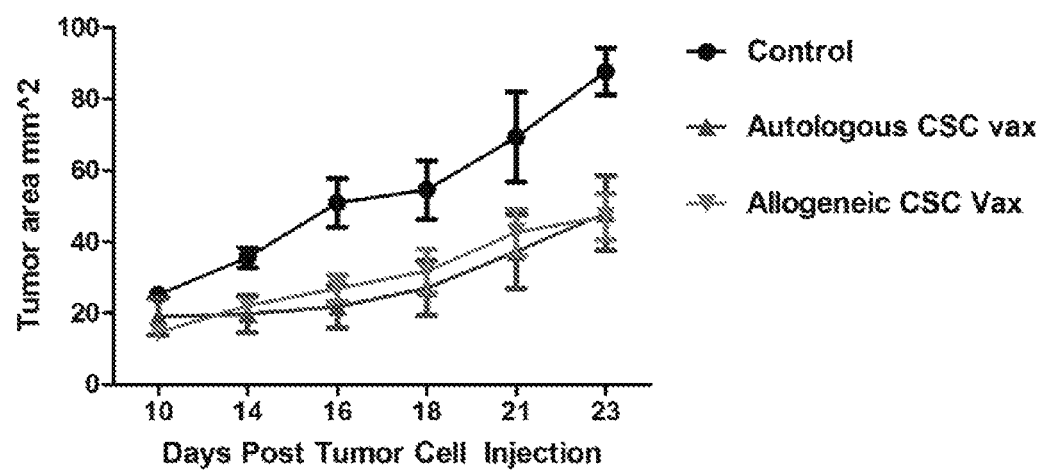
FIG. 8 is a graph showing that immunization with allogeneic CSC tumor lysates also generates protection. Mice with established sc PyMT tumors were immunized with CSC vaccines prepared from PyMT cells (Autologous CSC vax; triangles) or with CSC lysates from an unrelated tumor (4T1; Allogeneic CSC vax; upside-down triangles). Both vaccines generated equal levels of tumor protection, indicating that CSC vaccines can cross-protect against unrelated tumors.

Immunization with allogeneic CSC tumor lysates also generated protection. Mice with established sc PyMT tumors were immunized with CSC vaccines prepared from PyMT cells (Autologous CSC vax; triangles) or with CSC lysates from an unrelated tumor (4T1; Allogeneic CSC vax; upside-down triangles). Both vaccines generated equal levels of tumor protection, indicating that CSC vaccines can cross-protect against unrelated tumors (FIG. 8).

Figure 9:
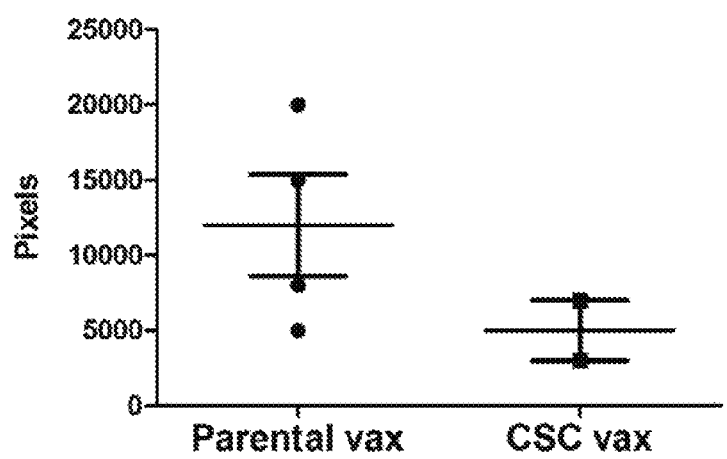
FIG. 9 is a graph showing that CSC vaccine induces depletion of cancer stem cells in tumor tissues. PyMT tumor tissues from mice that received a conventional tumor vaccine (Parental vax; circles) or a CSC vaccine (CSC vax; squares) were collected and immunostained for enumeration of the intensity of CD90 expression, a marker of tumor stem cells. Tumors in mice that received the CSC vaccine had much lower numbers of CD90+ CSC than mice vaccinated with a conventional tumor vaccine, indicative of immune destruction of the CSC in tumor tissues.

FIG. 9 is a graph showing that CSC vaccine induces depletion of cancer stem cells in tumor tissues. PyMT tumor tissues from mice that received a conventional tumor vaccine (Parental vax; circles) or a CSC vaccine (CSC vax; squares) were collected and immunostained for enumeration of the intensity of CD90 expression, a marker of tumor stem cells. Tumors in mice that received the CSC vaccine had much lower numbers of CD90+ CSC than mice vaccinated with a conventional tumor vaccine.

Figure 10:
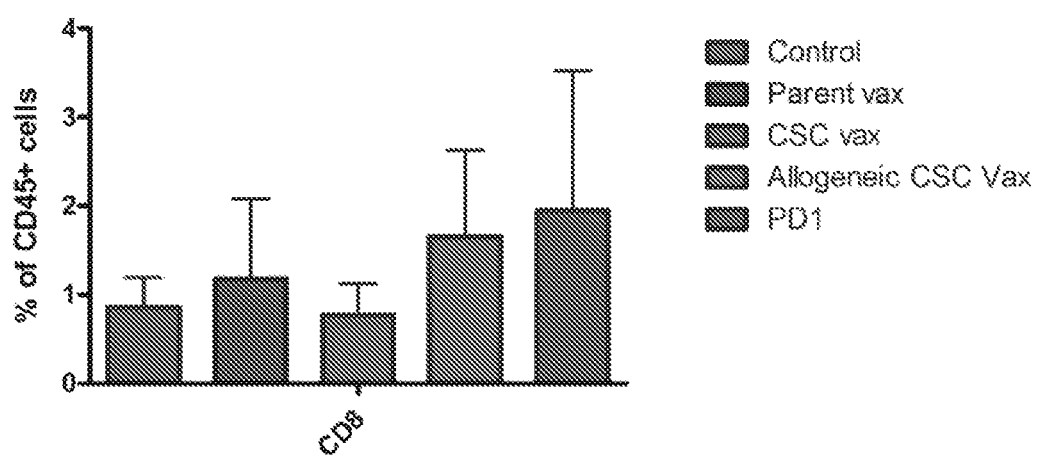
FIG. 10 is a graph showing that the allogeneic CSC vaccine induces CD8 T cell infiltration into tumor tissues. Tumor tissues from mice with PyMT tumors were collected following two immunizations with either non-CSC vaccines (parental vax), autologous CSC vaccines (CSC vax), or allogeneic CSC vaccines (allogeneic CSC vax), and evaluated for numbers of infiltrating CD45+CD8 T cells. As a positive control, mice were also treated with an antibody against the checkpoint molecule PD-1. The bars of the graph correspond from left to right to the legend from top to bottom. These studies indicate that therapeutic immunization with the CSC vaccine is equally as effective as treatment with a checkpoint inhibitor (i.e., PD-1 antibody treatment).

Allogeneic CSC vaccines induced CD8 T cell infiltration into tumor tissues. Tumor tissues from mice with PyMT tumors were collected following 2 immunizations with either non-CSC vaccines (parental vax), autologous CSC vaccines (CSC vax), or allogeneic CSC vaccines (allogeneic CSC vax), and evaluated for numbers of infiltrating CD45+ CD8 T cells. As a positive control, mice were also treated with an antibody against the checkpoint molecule PD-1. As shown in FIG. 10, allogeneic CSC vax induced CD8 T cell infiltration into tumor tissues, whereas autologous CSC vax did not. The bars of the graph correspond from left to right to the legend from top to bottom.

Example 3

CMC Enhances Response to Liposomal Immune Therapeutic

The ability of carboxy methylcellulose to enhance the immune response to liposomal immune therapeutics was demonstrated.

Mucosal immune stimulating complexes (cationic liposome DNA-pIC complexes (CLDPC)) were prepared that included cationic liposomes (DOTAP) in a 1:2 molar ratio with cholesterol, formulated as small unilamellar vesicles in dextrose solution. TLR agonists (PolyI:C and plasmid DNA in 1:1 ratio (by weight) were mixed with the liposomes to form complexes (100 ug pIC/DNA per 1 ml liposomes). Carboxy methylcellulose (CMC; low to mid-weight viscosity formulation; Sigma) was added to the liposome-TLR agonist complexes at 5-10% v/v final solution.

Figure 11:
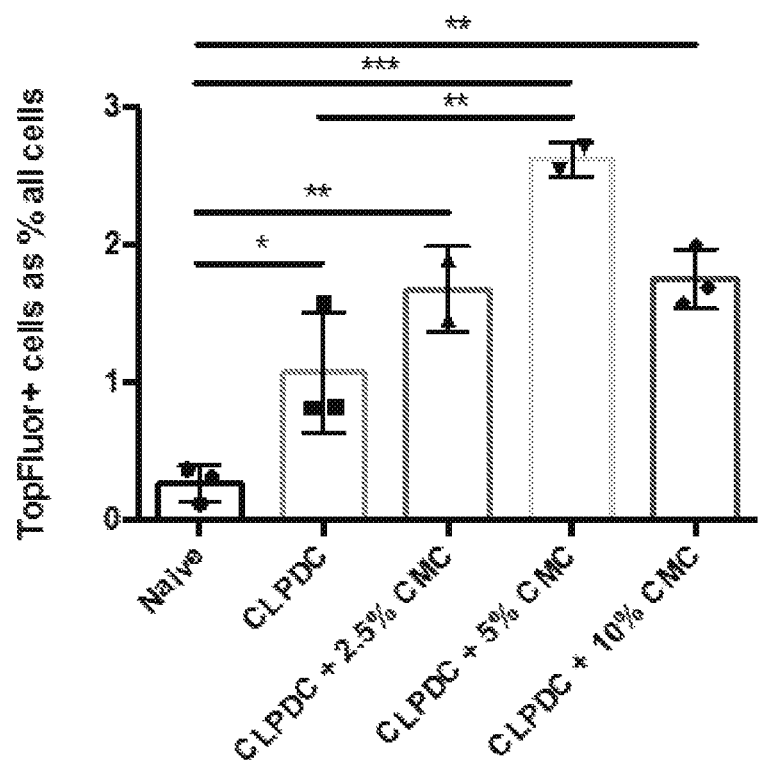
FIG. 11 is a graph showing enhanced liposome uptake in lymph nodes by addition of 5% carboxymethyl cellulose (CMC) to a CLPDC immunotherapeutic. The CLPDC immunotherapeutic consists of cationic liposomes complexed to a mixture of plasmid DNA and synthetic polyinosinic polycytidylic acid. Mice (n=3 per group) were immunized with 50 ul of cationic liposome DNA-pIC complexes (CLDPC) and trafficking of the liposomes to the nearest draining lymph node was assessed 24 h later, using flow cytometry. There were 5 groups of animals assessed: 1) naïve mice (control), not vaccinated; 2) mice immunized with CLDPC only; 3) mice immunized with CLDPC to which was added 2.5% (v/v) low molecular weight CMC; 4) mice immunized with CLDPC to which was added 5% (v/v) low molecular weight CMC; 5) mice immunized with CLDPC to which was added 210% (v/v) low molecular weight CMC. To allow tracking of the liposomes, liposomes that had the fluorescent dye TopFluor covalently attached to them were utilized. The percentage of lymph node cells that contained TopFluor$^+$ liposomes was determined by flow cytometry 24 h after s.c. vaccine administration.

Mice (n=3 per group) were immunized with 50 ul of cationic liposome DNA-pIC complexes (CLDPC) and trafficking of the liposomes to the nearest draining lymph node was assessed 24 h later, using flow cytometry. Five groups of animals were assessed: 1) naïve mice (control), not vaccinated; 2) mice immunized with CLDPC only; 3) mice immunized with CLDPC to which was added 2.5% (v/v) low molecular weight CMC; 4) mice immunized with CLDPC to which was added 5% (v/v) low molecular weight CMC; 5) mice immunized with CLDPC to which was added 210% (v/v) low molecular weight CMC. To allow tracking of the liposomes, liposomes that had the fluorescent dye TopFluor covalently attached to them were utilized. The percentage of lymph node cells that contained TopFluor+ liposomes was determined by flow cytometry 24 h after s.c. vaccine administration. The study found that addition of CMC at all three ratios tested (i.e., 2.5%, 5%, and 10%) significantly improved liposome trafficking to the lymph nodes compared to just the CLDPC complexes alone (FIG. 11). In addition, these studies clearly identified the addition of 5% CMC as superior in improving liposome uptake. These results are important because the more efficient uptake of the liposomes in the lymph nodes leads to greater immune activation and vaccine enhancement.

Figure 12:
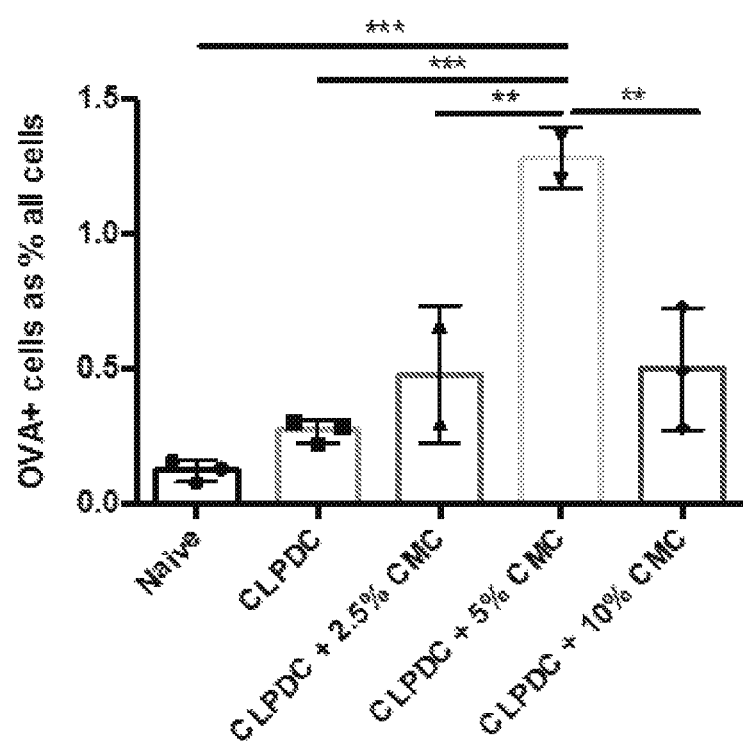
FIG. 12 is a graph showing enhanced antigen uptake in lymph nodes by addition of 5% CMC to CLPDC-adjuvanted vaccine. Mice (n=3 per group) were immunized with 50 ul of cationic liposome DNA-pIC complexes (CLDPC) that contained fluorescently-labeled antigen (ovalbumin) to allow detection of antigen trafficking and uptake by draining lymph nodes, using flow cytometry. For this study, 5 groups of animals assessed: 1) naïve mice (control), not vaccinated; 2) mice immunized with CLDPC only; 3) mice immunized with CLDPC to which was added 2.5% (v/v) low molecular weight CMC; 4) mice immunized with CLDPC to which was added 5% (v/v) low molecular weight CMC; 5) mice immunized with CLDPC to which was added 210% (v/v) low molecular weight CMC. The percentage of lymph node cells that contained labeled ovalbumin proteins (Ova$^+$ cells) was determined by flow cytometry 24 h after s.c. vaccine administration.

Mice (n=3 per group) were immunized with 50 ul of cationic liposome DNA-pIC complexes (CLDPC) that contained fluorescently-labeled antigen (ovalbumin) to allow detection of antigen trafficking and uptake by draining lymph nodes, using flow cytometry. For this study, 5 groups of animals assessed: 1) naïve mice (control), not vaccinated; 2) mice immunized with CLDPC only; 3) mice immunized with CLDPC to which was added 2.5% (v/v) low molecular weight CMC; 4) mice immunized with CLDPC to which was added 5% (v/v) low molecular weight CMC; 5) mice immunized with CLDPC to which was added 210% (v/v) low molecular weight CMC. The percentage of lymph node cells that contained labeled ovalbumin proteins (Ova$^+$ cells) was determined by flow cytometry 24 h after s.c. vaccine administration. The study found that addition of CMC at all three ratios tested (i.e., 2.5%, 5%, and 10%) significantly improved antigen uptake by cells in the draining lymph nodes compared to the uptake that was observed following administration of CLDPC complexes alone (FIG. 12). In addition, these studies clearly identified the addition of 5% CMC as superior in improving antigen delivery to lymph nodes. These results are important because the more efficient uptake of the antigen in lymph nodes leads to greater immune activation and vaccine enhancement.

Figure 13:
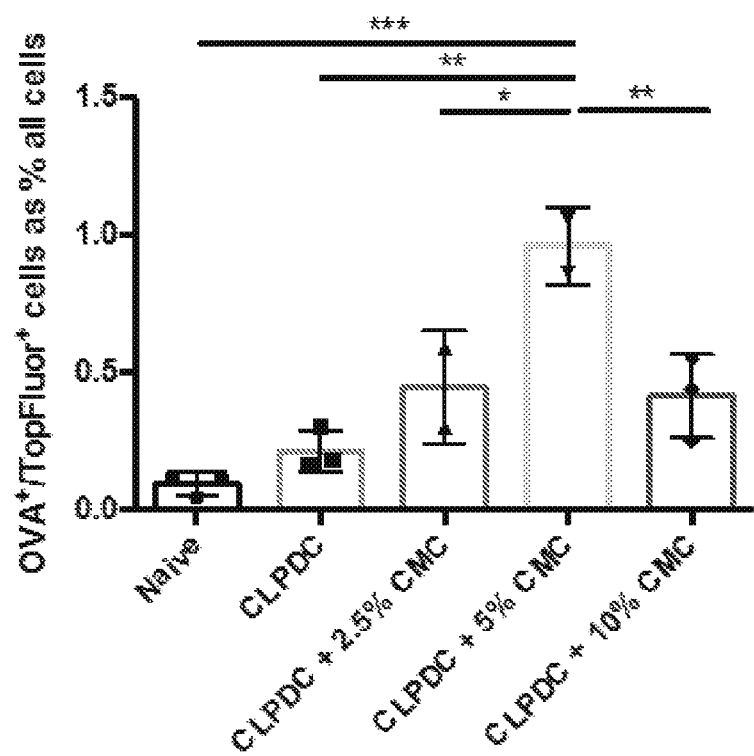
FIG. 13 is a graph showing enhanced simultaneous uptake of both liposomes and antigen by lymph node cells following vaccination with CLPDC and CMC complexes. Groups of mice were immunized with 50 ul vaccines containing labeled liposomes and labeled Ova antigen (different fluorescent dyes for each), as noted for FIGS. 11 and 12. This study allowed detection of cells that had taken up both the antigens and the liposomes. The results indicated that the addition of 5% CMC to the vaccine significantly enhanced uptake of liposomes and antigen by the same cells in the lymph nodes.

Groups of mice were immunized with 50 ul vaccines containing labeled liposomes and labeled Ova antigen (different fluorescent dyes for each), as described above. This study allowed detection of cells that had taken up both the antigens and the liposomes. The results indicated that the addition of 5% CMC to the vaccine significantly enhanced uptake of liposomes and antigen by the same cells in the lymph nodes (FIG. 13). This finding is important because dual uptake of both liposomes and antigen will lead to specific activation of the antigen presenting cells (e.g., dendritic cells and monocytes) that contain the antigens, followed by more effective presentation of the antigens to T cells in the lymph nodes.

Figure 14:
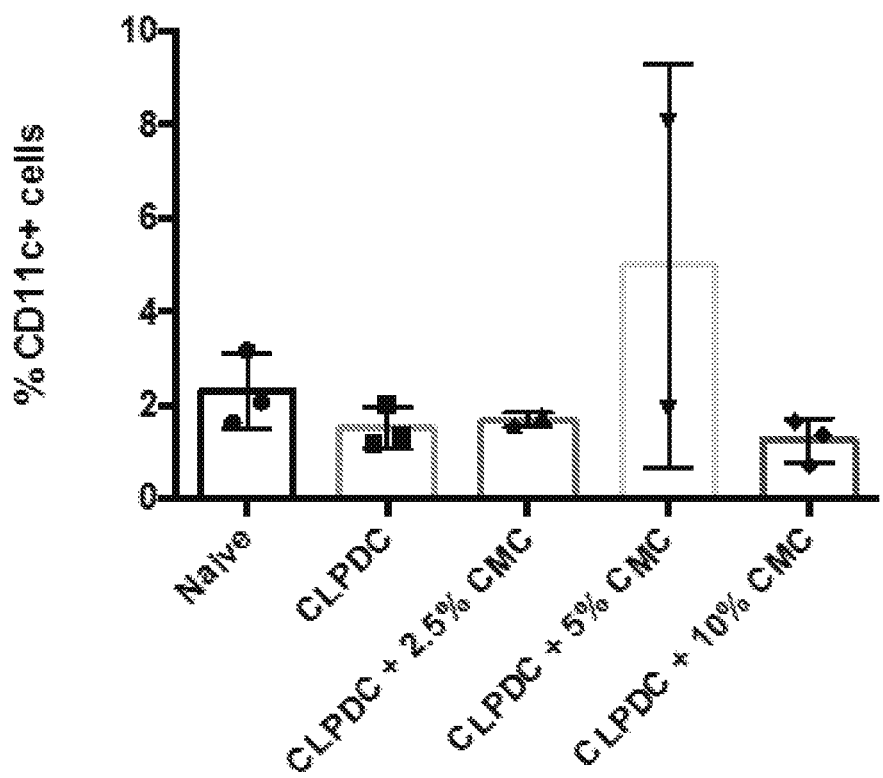
FIG. 14 is a graph showing administration of CLPDC immune therapeutic complexed to 5% CMC leads to greater accumulation of dendritic cells (DC) in draining lymph nodes. Mice were vaccinated with CLPDC complexes together with the indicated amounts of low-molecular weight CMC (as described in FIG. 11). 24 h later, the numbers of CD11c+ DC in the lymph nodes was quantitated by flow cytometry.

Mice were vaccinated with CLPDC complexes together with the indicated amounts of low-molecular weight CMC (as described above). 24 h later, the numbers of CD11c+ DC in the lymph nodes was quantitated by flow cytometry. Vaccination with CLDPC that contained 5% CMC led to a significant enhancement in DC entry into the lymph nodes, compared to mice immunized with CLDPC alone or with other amounts of CMC (FIG. 14). These findings are important because the greater numbers of DC in the lymph nodes leads to more efficient presentation of antigens to T cells, hence improved overall vaccine immunity.

Example 4

Stem Cell Cancer Vaccine Induces Unique Immune Responses

The immune response induced by a stem cell cancer vaccine of the present invention was characterized.

Mice (n=5 per group) were vaccinated three times with two different cancer vaccines, and pooled serum from the vaccinated mice was used to generate immunoblots against tumor antigens from PyMT tumor cells grown in vitro. The two cancer vaccines were prepared using tumor cell lysates prepared from: 1) mouse 4T1 breast cancer tumor cells grown in conventional medium under plastic adherence conditions ("Tumor vacc"); or 2) 4T1 cells enriched for cancer stem cells by culture under non-adherent conditions, using stem cell enrichment medium ("Stem cell vacc").

Figure 15:
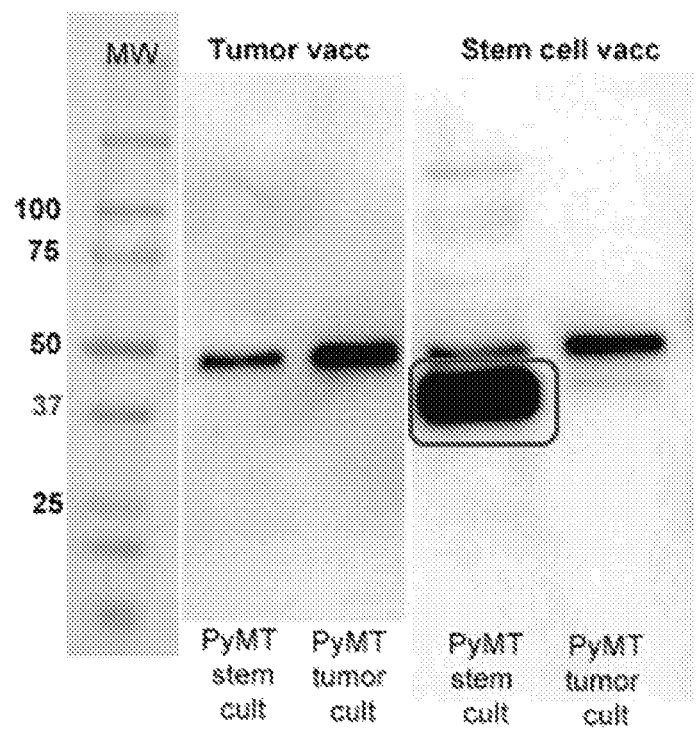
FIG. 15 depicts Western blot data identifying a unique approximately 40 kD protein induced by vaccination with the stem cell vaccine, but not by vaccination with a conventional tumor vaccine. These data also demonstrate that the protein is not expressed by tumor cells grown in vitro under non-stem cell conditions. The CSC vaccine induced immune response against this 40 kD protein is one explanation for the efficacy of CSC vaccines compared to conventional tumor lysate vaccines.

The tumor lysates for the Western blots were prepared from mouse PyMT breast cancer cells grown under conventional tumor cell conditions ("PyMT tumor cult"), or from tumor cells grown under stem cell enrichment conditions ("PyMT stem cult"). For each lane shown in FIG. 15, 3 ug tumor lysate was run on acrylamide gels, then proteins transferred to cellulose membranes, and blotted with serum from mice vaccinate with the conventional tumor vaccine ("Tumor vacc") or from serum with mice vaccinated with stem cell vaccines ("Stem vacc"), and specific recognition of tumor proteins was determined by anti-mouse secondary antibody and luminescence detection.

This study revealed that mice that received the stem cell vaccine developed antibody responses against a unique approximately 40 kD protein present in PyMT stem cell cultures, but not present in non-stem cell cultures. Moreover, mice that received the non-stem cell vaccine did not recognize the stem cell specific antigen. These findings suggest that the anti-tumor activity elicited by the stem cell vaccine may be mediated in part by immune responses (both cellular and humoral) against this 40 kD protein. Thus, recognition of this protein may represent a unique immune signature of the stem cell vaccine.

Figure 16:
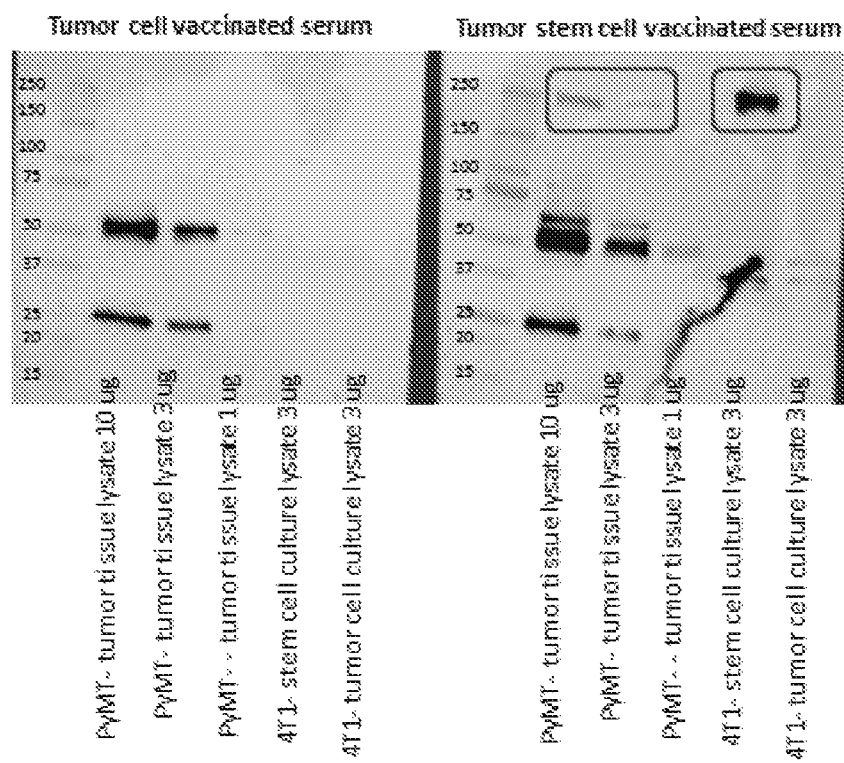
FIG. 16 depicts Western blot data identifying a unique approximately 250 kD protein induced by vaccination with the stem cell vaccine, but not by vaccination with a conventional tumor vaccine. These data also demonstrate that the protein is not expressed by tumor cells grown in vitro under non-stem cell conditions. However, this antigen is expressed by tumor cells growing in mice. The CSC vaccine induced immune response against this 250 kD protein is one explanation for the efficacy of CSC vaccines compared to conventional tumor lysate vaccines.

Cancer stem cell vaccine also induces a unique immune response against a second 250 kD protein. Mice were immunized with two different cancer vaccines, as described in FIG. 15, and serum from mice immunized with the conventional tumor cell vaccine (FIG. 16, left panel) and from the stem cell vaccine (FIG. 16, right panel) was used to immunoblot proteins from tumor tissues or in vitro cultured cells (x-axis). Lysates were prepared from mouse PyMT tumor tissues harvested from their SC location in unvaccinated mice ("PyMT tumor tissue lysate") and loaded in the indicated amounts in lanes on acrylamide gels. Lysates were also prepared from the mouse tumor cell line 4T1 (which was used to prepare the tumor vaccines). The 4T1 tumor cell line was cultured under standard tumor cell conditions ("tumor cell culture") or under stem cell conditions ("stem cell culture"), as described in FIG. 15.

These studies revealed that serum from mice vaccinated with the stem cell vaccine (right panel) contained antibodies specific for a protein of approximately 250 kD mass, present in both PyMT tumor tissues, and in 4T1 cells grown under stem conditions (two red boxes). Importantly, this protein was not present in 4T1 cells grown under non-stem condition. In addition, serum from mice that were vaccinated with lysates prepared from 4T1 cells grown under tumor cell culture conditions (i.e., non-stem conditions) did not recognize this 250 kD protein.

These results indicate therefore that the cancer stem cell vaccines of the present invention induce a unique immune response against a second protein that appears to be expressed by tumor cells cultured under stem cell conditions. Importantly, this protein is also expressed by tumor tissues from live animals, including tumors unrelated to the tumor cells from which the original vaccine was prepared. These findings suggest that the anti-tumor activity elicited by the stem cell vaccine may be mediated in part by immune responses (both cellular and humoral) against this 250 kD protein. Thus, recognition of this protein may represent another unique immune signature of the stem cell vaccine.

All of the U.S. patents, U.S. patent application publications, U.S. patent applications, foreign patents, foreign patent applications and non-patent publications referred to in this specification and/or listed in any Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention.

What is claimed:

1. An immunogenic composition, comprising: a cancer stem cell (CSC) lysate from spheroid CSC-enriched cultures obtained from non-adherent, serum-free tumor cell spheroid cultures from established tumor cell lines, wherein the spheroid cultures of the CSCs comprise elevated expression of ALDH compared to the established tumor cell line cells not cultured in serum-free medium and not under non-adherent culture conditions; and at least one adjuvant, the at least one adjuvant comprises cationic liposome-DNA complex (CLDC), cationic liposome DNA-pIC complex (CLDPC), or a combination thereof wherein the immunogenic composition does not include dendritic cells.

2. The immunogenic composition according to claim 1, wherein elevated ALDH is 1.1-fold or more in the spheroid CSC cultures compared to the same established tumor cell line cells not cultured in serum-free medium and under non-adherent conditions.

3. The immunogenic composition according to claim 1, wherein the spheroid cultures of the established tumor cell line derived CSCs further comprise elevated expression of at least one of CD90 and CD117 compared to the established tumor line cells not cultured in serum-free medium under non-adherent culture conditions.

4. The immunogenic composition according to claim 1, wherein the established tumor cell line derived CSCs are derived from a tumor of a subject having at least one condition comprising a small-cell lung cancer, non-small cell lung cancer, cancer of the peritoneum, hepatic carcinoma, colon cancer, melanoma, glioma, Waldenstrom's Macroglobulinemia, or combinations thereof.

5. The immunogenic composition according to claim 1, wherein the composition consists essentially of a cancer stem cell (CSC) lysate derived from established tumor cell line cells cultured to enrich for spheroid CSC-enriched cultures obtained from non-adherent, serum-free solid tumor cell spheroid cultures; at least one adjuvant, the at least one adjuvant comprising cationic liposome-DNA complex (CLDC); and at least one agent capable of blocking recruitment of, or reducing migration of monocytes.

6. The immunogenic composition according to claim 1, wherein the CSCs of the CSC lysate further comprise elevated expression of one or more of CD90, CD117, Sca1, CD133, CD34, CD73, Nanog, Klf-4, and Oct3/4 compared to adherent, serum cultured tumor cell cultures.

7. The immunogenic composition according to claim 1, wherein the cancer stem cell lysate is obtained from cancer stem cells having undergone at least one of one or more freeze-thaw cycles.

8. The immunogenic composition according to claim 1, wherein the cancer stem cell lysate is derived from established tumor cell lines, originally generated from at least one cancer type comprising lung cancer, stomach cancer, esophageal cancer, pancreatic cancer, brain cancer, cervical cancer, ovarian cancer, liver cancer, bladder cancer, breast cancer, colorectal cancer, uterine carcinoma, salivary gland carcinoma, kidney cancer, skin cancer, prostate cancer, vulvar cancer, thyroid cancer, head and neck cancer, or combinations thereof.

9. The immunogenic composition according to claim 1, wherein the at least one adjuvant is a cationic liposome-DNA complex (CLDC).

10. The immunogenic composition according to claim 1, wherein the CSC lysate comprises from about 50 µgs to about 500 µgs of protein.

11. The immunogenic composition according to claim 1, further comprising at least one agent capable of blocking recruitment of or reducing migration of monocytes.

12. The immunogenic composition according to claim 11, wherein the at least one agent capable of blocking recruitment of or reducing migration of monocytes comprises at least one agent capable of reducing the activation of, or blocking an angiotensin II receptor (ARB) comprising at least one of losartan, azilsartan, candesartan, eprosartan, irbesartan, olmesartan, telmisartan, and valsartan, or a combination thereof.

13. The immunogenic composition according to claim 11, wherein the at least one agent capable of blocking recruitment of or reducing migration of monocytes comprises at least one agent capable of reducing activation of, or blocking activation of a C—C chemokine receptor type 2 (CCR2).

14. A pharmaceutical composition comprising the immunogenic composition according to claim 1, and a pharmaceutically acceptable excipient.

15. The pharmaceutical composition according to claim 14, wherein the pharmaceutical composition is formulated for administration to a subject for delivery subcutaneously, intramuscularly, intradermally, intravenously, intranasally, or intraarterially.

16. A kit comprising at least one immunogenic composition according to claim 1, and at least one container.

* * * * *